US009526747B2

(12) United States Patent
Verfaillie et al.

(10) Patent No.: US 9,526,747 B2
(45) Date of Patent: *Dec. 27, 2016

(54) USE OF MULTIPOTENT ADULT STEM CELLS IN TREATMENT OF MYOCARDIAL INFARCTION AND CONGESTIVE HEART FAILURE

(75) Inventors: Catherine M. Verfaillie, St. Paul, MN (US); Morayma Reyes, Sammamish, WA (US); Leo T. Furcht, Golden Valley, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 672 days.

This patent is subject to a terminal disclaimer.

(21) Appl. No.: 13/301,186

(22) Filed: Nov. 21, 2011

(65) Prior Publication Data

US 2012/0064047 A1 Mar. 15, 2012

Related U.S. Application Data

(63) Continuation of application No. 11/151,689, filed on Jun. 13, 2005, now Pat. No. 8,075,881, which is a continuation-in-part of application No. 10/963,444, filed on Oct. 11, 2004, now abandoned, which is a continuation-in-part of application No. 10/048,757, filed as application No. PCT/US00/21387 on Aug. 4, 2000, now Pat. No. 7,015,037, said application No. 10/963,444 is a continuation-in-part of application No. 10/467,963, filed as application No. PCT/US02/04652 on Feb. 14, 2002, now Pat. No. 7,838,289.

(60) Provisional application No. 60/147,324, filed on Aug. 5, 1999, provisional application No. 60/164,650, filed on Nov. 10, 1999, provisional application No. 60/268,786, filed on Feb. 14, 2001, provisional application No. 60/269,062, filed on Feb. 15, 2001, provisional application No. 60/310,625, filed on Aug. 7, 2001, provisional application No. 60/343,836, filed on Oct. 25, 2001.

(51) Int. Cl.
*A61K 35/12* (2015.01)
*A61P 9/00* (2006.01)
*C12N 5/074* (2010.01)
*A61K 35/34* (2015.01)

(52) U.S. Cl.
CPC ............ *A61K 35/34* (2013.01); *C12N 5/0607* (2013.01); *A61K 2035/124* (2013.01); *C12N 2500/36* (2013.01); *C12N 2500/38* (2013.01); *C12N 2501/105* (2013.01); *C12N 2501/11* (2013.01); *C12N 2501/135* (2013.01); *C12N 2501/235* (2013.01); *C12N 2501/33* (2013.01); *C12N 2501/39* (2013.01); *C12N 2533/52* (2013.01)

(58) Field of Classification Search
None
See application file for complete search history.

(56) References Cited

U.S. PATENT DOCUMENTS

| 5,486,359 | A | 1/1996 | Caplan et al. |
|---|---|---|---|
| 5,827,735 | A | 10/1998 | Young et al. |
| 6,090,625 | A | 7/2000 | Abuljadayel |
| 6,387,369 | B1 * | 5/2002 | Pittenger et al. ............ 424/93.7 |
| 7,514,074 | B2 | 4/2009 | Pittenger et al. |
| 8,268,619 | B2 * | 9/2012 | Giacomello et al. ......... 435/377 |
| 2002/0061587 | A1 | 5/2002 | Anversa |
| 2002/0164794 | A1 | 11/2002 | Wernet |
| 2003/0003090 | A1 | 1/2003 | Prockop et al. |
| 2003/0059414 | A1 | 3/2003 | Ho et al. |
| 2003/0103951 | A1 | 6/2003 | Pittenger |
| 2004/0235165 | A1 | 11/2004 | Prockop et al. |
| 2005/0169896 | A1 | 8/2005 | Li et al. |
| 2007/0003530 | A1 | 1/2007 | Pittenger |
| 2009/0214493 | A1 | 8/2009 | Pittenger |
| 2010/0172884 | A1 | 7/2010 | Pittenger |
| 2011/0158964 | A1 | 6/2011 | Pittenger |
| 2011/0158965 | A1 | 6/2011 | Pittenger |
| 2012/0021019 | A1 * | 1/2012 | Giacomello et al. ......... 424/400 |
| 2012/0141437 | A1 | 6/2012 | Pittenger |
| 2012/0141438 | A1 | 6/2012 | Pittenger |
| 2012/0148545 | A1 | 6/2012 | Pittenger |
| 2012/0207716 | A1 | 8/2012 | Pittenger |
| 2012/0213749 | A1 | 8/2012 | Pittenger |
| 2012/0263682 | A1 | 10/2012 | Pittenger |
| 2012/0269784 | A1 | 10/2012 | Pittenger |

FOREIGN PATENT DOCUMENTS

| WO | WO 95/14079 | 5/1995 |
|---|---|---|
| WO | WO 96/16163 | 5/1996 |
| WO | WO 99/16863 | 4/1999 |
| WO | WO 01/21766 | 3/2001 |
| WO | WO 01/21767 | 3/2001 |
| WO | WO 01/62901 | 8/2001 |

OTHER PUBLICATIONS

Kolf et al (Arthritis Research & Therapy vol. 9 2007.*
Bianco et al., "Stem cells in tissue engineering" Nature; 414:118-121 (2001).
Lovell-Badge et al., "The future for stem cell research" Nature; 414:88-91 (2001).
Donovan et al., "The end of the beginning for pluripotent stem cells" Nature; 414:92-97 (2001).
Spradling et al., "Stem cells find their niche" Nature, 414:98-104 (2001).
Hamilton, D., "The tissue bank's shakey underpinnings" Science; 257:869 (1992).

(Continued)

*Primary Examiner* — David Berke-Schlessel
(74) *Attorney, Agent, or Firm* — Tarolli, Sundheim, Covell, Tummino LLP

(57) ABSTRACT

The invention provides isolated stem cells of non-embryonic origin that can be maintained in culture in the undifferentiated state or differentiated to form cells of multiple tissue types. Also provided are methods of isolation and culture, as well as therapeutic uses for the isolated cells in cardiac indications.

7 Claims, 7 Drawing Sheets

(56) References Cited

OTHER PUBLICATIONS

Figure 1:
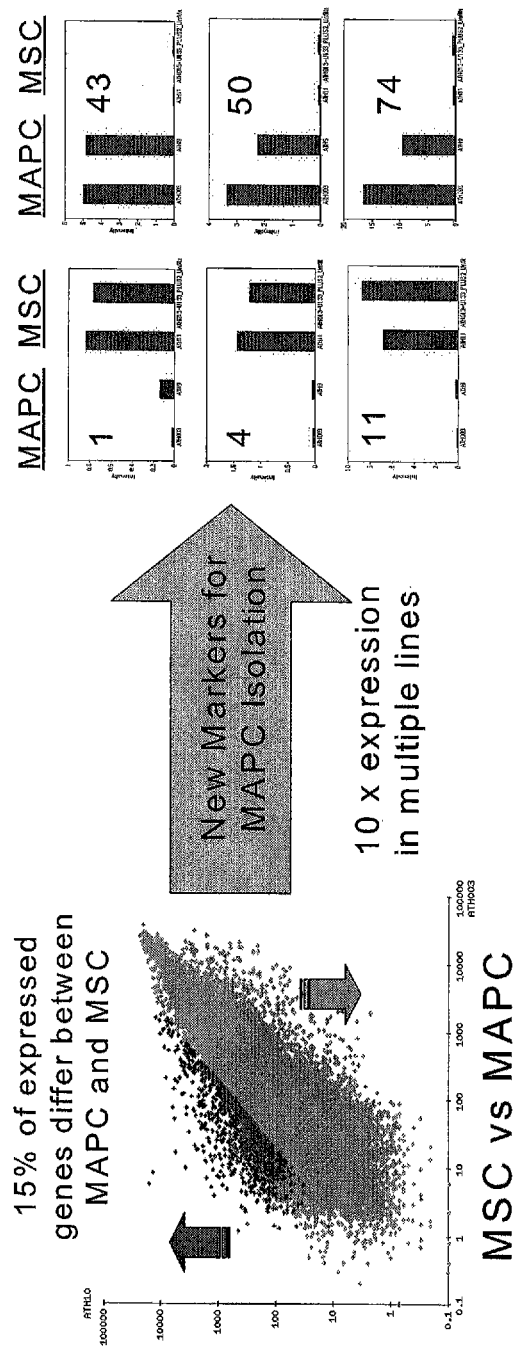

Soonpaa et al., "Formation of nascent intercalated disks between grafted fetal cardiomyocytes and host myocardium" Science; 264:98-101 (1994).
Prockop, D., "Marrow stromal cells as stem cells for nonhematopoietic tissues" Science; 276:71-74 (1997).
Bjornson et al., "Turning brain into blood: a hematopoietic fate adopted by adult neural stem cells in vivo" Science; 283:534-537 (1999).
Reyes et al., "Purification and ex vivo expansion of postnatal human marrow mesodermal progenitor cells" Blood; 98:2615-2625 (2001).
Lowell, S., "Stem cells show their potential" Trends in Cell Biology; 10:210-211 (2000).
Asahara et al., "Stem cell therapy and gene transfer for regeneration" Gene Therapy; 7:451-457 (2000).
Koh et al., "Differentiation and long-term survival of C2C12 myoblast grafts in heart" J. Clin. Invest.; 92:1548-54 (1993).
Koh at al., "Strategies for myocardial repair" J. Interven. Cardio.; 8:387-393 (1995).
Dewitt, N., "Nature insight. Stem cells" Macmillan Magazines Lts. 2001, p. 87.
Orlic, et al., "Bone marrow cells regenerate infarcted myocardium" Nature; 410:701-5 (2001).
Beltrami et al., "Evidence that human cardiac myocytes divide after myocardial infarction" N. Engl. J. Med.; 344:1750-7 (2001).
Kehat et al., "Human embryonic stem cells can differentiate into myocytes with structural and functional properties of cardiomyocytes" J. Clin. Invest.; 108:407-414 (2001).
Reyes et al., "Origin of endothelial progenitors in human postnatal bone marrow" J. Clin. Invest.; 109:1-10 (2002).
Smith, A., "Cell therapy: in search of pluripotency" Current Biology; 8:R802-804 (1998).
Reyes et al., "Characterization of multilineage mesodermal progenitor cells in adult marrow" Abstract No. 124, American Society for Hematology (2001).
Reyes et al., "Turning marrow into brain: generation of glial and neuronal cells from adult bone marrow mesencymal stem cells" Abstract No. 1676, American Society for Hematology (2001).
Reyes et al., "Skeletal smooth and cardiac muscle differentiation from single adult marrow derived mesodermal progenitor cells" Abstract No. 2610, American Society for Hematology (2001).
Reyes et al., "Endothelial cells generated from human marrow derived mesenchymal stem cells (MSC)" Abstract No. 2276, American Society for Hematology (2001).
Thompson, L., "Fetal transplants show promise" Science; 257:868-869 (1992).
Verfaillie, C. "Investigator Profile" Journal of Hematotherapy and Stem Cell Research; 11:441-444 (2002).
Verfaillie et al., "Stem cells: hype and reality" Hematology (Am Soc Hematol Educ Program); 369-391 (2002) PMID: 12446433 [PubMed—in process].
Verfaillie, C.M., "Meeting Report on an NHLBI Workshop on ex vivo expansion of stem cells, Jul. 29, 1999, Washington D.C. National Heart Lung and Blood Institute" Exp. Hematol.; 28:361-4 (2000).
Pagen Westphal, S., "Adult bone marrow eyed as source of stem cells" Boston Globe, Jan. 24, 2002.
Pagen Westphal, S., "Ultimate stem cell discovered" New Scientist, Jan. 23, 2002.
Wade et al., "Scientists herald a versatile adult cell" The New York Times on the Web, Jan. 25, 2002.
Pittenger et al., "Multilineage potential of adult human mesenchymal stem cells" Science, U.S. American Associate for the Advancement of Science; 284:143-147 (1999).
Reyes et al., "Characterization of multipotent adult progenitor cells, a subpopulation of mesenchymal stem cells" Annals of the New York Academy of Science; 938:231-235.
Geissler et al., "Effective use of donor MHC class I gene therapy in organ transplantation: prevention of antibody-mediated hyperacute heart allograft rejection in highly sensitized rat recipients" Human Gene Therapy; 11:459-469 (1999).
Eglitis et al., "Hematopoletic cells differentiate into both microglia and macroglia in the brains of adult mice" Proc Natl Acad Sci USA; 94:4080-4085 (1997).
Kopen et al., "Marrow stromal cells migrate throughout forebrain and cerebellum, and they differentiate into astrocytes after injection into neonatal mouse brains" Proc Natl Acad Sci USA; 96:10711-10716 (1999).
Lagasse et al., "Purified hematopoletic stem cells can differentiate into hepatocytes in vivo" Nature Medicine; 6:1229-1234 (2000).
Wang et al., "Cell fusion is the principal source of bone-marrow-derived hepatocytes" Nature; 422:897-901 (2003).
Young et al., "Human reserve pluripotent mesenchymal stem cells are present in the connective tissues of skeletal muscle and dermis derived from fetal, adult, and geriatric donors" The Anatomical Record; 264:51-62 (2001).
Woodbury et al., "Adult rat and human bone marrow stromal cells differentiate into neurons" J. Neurosci. Res.; 61:364-370 (2000).
Lee et al., "In vitro hepatic differentiation of human mesenchymal stem cells" Hepatology; 40:1276-1284 (2004).
Check "Stem cell paper corrected" Nature; 447:763 (2007) and Jiang et al., "Pluripotency of mesenchymal stem cells derived from adult bone marrow" Erratum in Nature; 447:879-880 (2007).
Noonan, "Limitations on the usefulness of adult stem cells" Patent Docs; (Feb. 28, 2007).
Pincock, "Adult stem cell report questioned" The Scientist; (Feb. 26, 2007).
Serafini et al., "Hematopoietic reconstitution by multipotent adult progenitor cells: precursors to long-term hematopoietic stem cells" J. Exp. Med.; 204:129-39 (2007).
Brazelton et al., "From marrow to brain: expression of neuronal phenotypes in adult mice" Science; 290:1775-9 (2000).
Clarke et al,. "Generalized potential of adult neural stem cells" Science; 288: 1660-3 (2000).
Johansson et al., "Neural stem cells in the adult human brain" Exp. Cell. Res.; 253:733-6 (1999).
Mezey et al., "Turning blood into brain: cells bearing neuronal antigens generated in vivo from bone marrow" Science; 290:1779-82 (2000).
Morshead et al., "Hematopoietic competence is a rare property of neural stem cells that may depend on genetic and epigenetic alterations" Nat. Med.; 8:268-73 (2002).
Petersen et al., "Bone marrow as a potential source of hepatic oval cells" Science; 284:1168-70 (1999).
Sanchez-Ramos et al., "Adult bone marrow stromal cells differentiate into neural cells in vitro" Exp. Neurol.; 164:247-56 (2000).
Scintu et al., "Differentiation of human bone marrow stem cells into cells with a neural phenotype: diverse effects of two specific treatments" BMC Neurosci.; 7:14 (2006).
Nagaya et al., "Intravenous administration of mesenchymal stem cells improves cardiac function in rats with actue myocardial infarction through angiogenesis and myogenesis" Am. J. Physiol. Heart Circ. Phyiol.; 287:H2670-H2676 (2004).
Freyman et al., "A quantitative, randomized study evaluating three methods of mesenchymal stem cell delivery following myocardial infarction" European Heart Journal; 27:1114-1122 (2006).
Dai et al., "Allogeneic mesenchymal stem cell transplantation in postinfarcted rat myocardium. Short- and long-term effects" Circulation; 112:214-223 (2005).
Kim et al., "Cell transplantation improves ventricular function after a myocardial infarction: a preclinical study of human unrestricted somatic stem cells in a porcine model" Circulation;112: I96-I104 (2005).
Amado et al., "Cardiac repair with intramyocardial injection of allogeneic mesenchymal stem cells after myocardial infarction" PNAS; 102:11474-11479 (2005).
Pelacho et al., "Multipotent adult progenitor cell transplantation increases vascularity and improves left ventricular function after myocardial infarction" J. Tissue Eng. Regen. Med; 1:51-59 (2007).
Izadpanah et al., "Biologic properties of mesenchymal stem cells derived from bone marrow and adipose tissue" Journal of Cellular Biochemistry; 99:1285-1297 (2006).

(56) References Cited

OTHER PUBLICATIONS

Long et al., "Neural cell differentiation in vitro from adult human bone marrow mesenchymal stem cells" Stem Cells and Development; 14;65-69 (2005).
Moriscot et al., "Human bone marrow mesenchymal stem cell can express insulin and key transcription factors of the endocrine pancrease developmental pathway upon genetic and/or microenvironmental manipulation in vitro" Stem Cells; 23:594-604 (2005).
Sanchez-Ramos et al., "Adult bone m arrow stromal cells differentiate into neural cells in vitro" Exp. Neurol.; 164:247-56 (2000).
U.S. Patent and Trademark Office, Office Action dated Apr. 3, 2007, in related U.S. Appl. No. 11/238,234.
Giles, J., "The trouble with replication" Nature, 422:344-347 (2006).
Verfaillie, C.M., Multipotent adult progenitor cells: an Update Novartis Found Symp, 254:55-65 (2005).
Verfaillie, C.M., Multipotent adult progenitor cells: an update: Novartis Found Symp., 254:55-65 (2005).
Aldhous et al., "Fresh questions on stem cell findings" New Scientist, Mar. 21, 2007.
Liedtke, S., et al. Oct4 expression revisited; potential pitfalls for data misinterpretation in stem cell research. Biol. Chem., (2008) vol. 389, pp. 845-850.
Atlasi, Y., et al. Oct4 Spliced Variants are Differentially Expressed in Human Pluripotent and Nonpluripotent Cells. Stem Cells, (2008) vol. 26, pp. 3068-3074.
Moriscot, C., et al. Human bone marrow mesenchymal stem cells can express insulin and key transcription factors of the endocrine pancreas developmental pathway upon genetic and/or micro-environmental manipulation in vitro. Stem Cells, (2005) vol. 23, pp. 594-603.
Roche, S., et al. Oct-4, Rex-1, and Gata-4 expression in human MSC increase the differentiation efficiency but not hTERT expression. J. Cell. Biochem. (2007) vol. 101, pp. 271-280.
Tai, M.H., et al. Oct4 expression in adult human stem cells: evidence in support of the stem cell theory of carcinogenesis. Carcinogenesis (2005) vol. 26, pp. 495-502.
Tondreau, T., et al. Mesenchymal stem cells derived from CD133-positive cells in mobilized peripheral blood and cord blood: proliferation, Oct4 expression, and plasticity. Stem Cells (2005) vol. 23, pp. 1105-1112.
Takeda, J., et al. Human Oct3 gene family: cDNA sequences, alternative splicing, gene organization chromosomal location, and expression at low levels in adult tissues. Nucleic Acids Research (1992) vol. 20, No. 17, pp. 4613-4620.
Brehm, A., et al. The Carboxy-Terminal Transactivation Domain of Oct-4 Acquires Cell Specificity through the POU Domain. Mol. Cell. Biol. (1997) vol. 17, No. 1, pp. 154-162.
Jiang, Y., et al. Pluripotency of mesenchymal stem cells derived from adult marrow. Nature (2002) vol. 418, pp. 41-49.
Decision on Motions; Patent Interference No. 105,953 SGL, Tech Center 1600; filed Sep. 26, 2014.
Aldous et al., "Flawed stem cell data withdrawn" New Scientist; (Feb. 15, 2007).
Jiang et al., "Multipotent progenitor cells can be isolated from postnatal murine bone marrow, muscle, and brain" Exp. Hematol.; 30:896-904 (2002).
Jiang et al., "Pluripotency of mesenchymal stem cells derived from adult marrow" Nature; 418:41-49 (2002).
Aldous et al., "Fresh questions on stem cell findings" New Scientist; (Mar. 24, 2007).
Reyes et al., "Purification and ex vivo expansion of postnatal human marrow mesodermal progenitor cells" Blood; 98:2615-25 (2001).
Check "Stem cell paper corrected" Nature; 447:763 (2007) and Jiang et al., "Pluripotency of mesenchymal stem cells derived from adult bone marrow" Erratum in Nature; 447:879.
Chi, "Adult stem cell figure retracted" The Scientist; (Jun. 13, 2007).
Glenn, "Paper on versatility of adult stem cells comes under question" The Chronicle; (Feb. 26, 2007).
Holden, "Stem Cells. Controversial marrow cells coming into their own?" Science; 315:760-761 (2007).
Lerner et al., "Stem cell study was flawed, U panel finds" Star Tribune; (Feb. 27, 2007).
Noonan, "Limitations on the usefulness of adult stem cells" Patent Docs (Feb. 28, 2007).
Pincock, "Adult stem cell report questioned" The Scientist (Feb. 26, 2007).
Serafini et al., "Hematopoietic reconstitution by multipotent adult progenitor cells: precursors to long-term hematopoietic stem cell" J. Exp. Med.; 204:129-139 (2007).
Verfaillie, "Letter to the Editor" Experimental Hematology; (2007).
Jiang et al., "Pluripotency of mesenchymal stem cells derived from adult marrow, Supplemental Information for Verfaillie Corrigendum" Nature; 418:41-49 (2002).
Office Action and 892 dated Apr. 7, 2008 in related U.S. Appl. No. 11/151,689.
Strauer, et al., "Repair of Infarcted Myocardium by Autologous Intracoronary Mononuclear Bone Marow Cell Transplanation in Humans" Circulation 106:1913-1918 (2002).

\* cited by examiner

Phase III: (a) IV injection of allo rMAPC; (b) Direct injection in CHF model (30 days post-MI)

USE OF MULTIPOTENT ADULT STEM CELLS IN TREATMENT OF MYOCARDIAL INFARCTION AND CONGESTIVE HEART FAILURE

RELATED APPLICATIONS/PATENTS

This application is a continuation of U.S. application Ser. No. 11/151,689, filed Jun. 13, 2005 (allowed), which is a continuation-in-part of U.S. application Ser. No. 10/963,444, filed Oct. 11, 2004, which is a continuation-in-part of U.S. application Ser. No. 10/048,757 filed Feb. 1, 2002 which is a U.S. National Stage Application of PCT/US00/21387 filed Aug. 4, 2000 and published in English as WO 01/11011 on Feb. 15, 2001, which claims priority under 35 U.S.C. 119(e) from U.S. Provisional Application No. 60/147,324 filed Aug. 5, 1999 and 60/164,650 filed Nov. 10, 1999. U.S. application Ser. No. 10/963,444, filed Oct. 11, 2004, is also a continuation-in-part of U.S. application Ser. No. 10/467,963 filed on Aug. 11, 2003 which is a U.S. National Stage Application of PCT/US02/04652 filed Feb. 14, 2002 and published in English as WO 02/064748 on Aug. 22, 2002, which claims priority under 35 U.S.C. 119(e) from U.S. Provisional Application No. 60/268,786 filed Feb. 14, 2001; 60/269,062 filed Feb. 15, 2001; 60/310,625 filed Aug. 7, 2001; and 60/343,836 filed Oct. 25, 2001, which applications and publications are herein incorporated by reference.

FIELD OF THE INVENTION

The field of the invention is alleviating the symptoms of heart damage, especially resulting from myocardial infarction, by administering multipotent adult stem cells.

BACKGROUND OF THE INVENTION

Stem Cells

The embryonal stem (ES) cell has unlimited self-renewal and can differentiate into all tissue types. ES cells are derived from the inner cell mass of the blastocyst or primordial germ cells from a post-implantation embryo (embryonal germ cells or EG cells). ES and EG cells have been derived from mouse, and, more recently, from non-human primates and humans. When introduced into blastocysts, ES cells can contribute to all tissues. A drawback to ES cell therapy is that, when transplanted in post-natal animals, ES and EG cells generate teratomas.

ES (and EG) cells can be identified by positive staining with antibodies to SSEA1 (mouse) and SSEA4 (human). At the molecular level, ES and EG cells express a number of transcription factors specific for these undifferentiated cells. These include Oct-4 and rex-1. Also found are the LIF-R (in mouse) and the transcription factors sox-2 and rox-1. Rox-1 and sox-2 are also expressed in non-ES cells. A hallmark of ES cells is the presence of telomerase, which provides these cells with an unlimited self-renewal potential in vitro.

Oct-4 (Oct 3 in humans) is a transcription factor expressed in the pregastrulation embryo, early cleavage stage embryo, cells of the inner cell mass of the blastocyst, and in embryonic carcinoma (EC) cells (Nichols J, et al (1998) Cell 95:379-91), and is down-regulated when cells are induced to differentiate. Expression of Oct-4 plays an important role in determining early steps in embryogenesis and differentiation. Oct-4, in combination with Rox-1, causes transcriptional activation of the Zn-finger protein Rex-1, also required for maintaining ES undifferentiated (Rosfjord E, Rizzino A. (1997) Biochem Biophys Res Commun 203:1795-802; Ben-Shushan E, et al (1998) Mol Cell Biol 18:1866-78). In addition, sox-2, expressed in ES/EC, but also in other more differentiated cells, is needed together with Oct-4 to retain the undifferentiated state of ES/EC (Uwanogho D et al (1995) Mech Dev 49:23-36). Maintenance of murine ES cells and primordial germ cells requires LIF.

The Oct 4 gene (Oct 3 in humans) is transcribed into at least two splice variants in humans, Oct 3A and Oct 3B. The Oct 3B splice variant is found in many differentiated cells whereas the Oct 3A splice variant (also previously designated Oct 3/4) is reported to be specific for the undifferentiated embryonic stem cell. See Shimozaki et al (2003) Development 130:2505-12.

Adult stem cells have been identified in most tissues. Hematopoietic stem cells are mesoderm-derived and have been purified using cell surface markers and functional characteristics. The hematopoietic stem cell, isolated from bone marrow, blood, cord blood, fetal liver and yolk sac, is the progenitor cell that reinitiates hematopoiesis and generates multiple hematopoietic lineages. Hematopoietic stem cells can repopulate the erythroid, neutrophil-macrophage, megakaryocyte and lymphoid hematopoietic cell pool. Stem cells that differentiate only to form cells of hematopoietic lineage, however, are unable to provide a source of cells for repair of other damaged tissues, for example, heart.

Neural stem cells were initially identified in the subventricular zone and the olfactory bulb of fetal brain. Studies in rodents, non-human primates and humans, have shown that stem cells continue to be present in adult brain. These stem cells can proliferate in vivo and continuously regenerate at least some neuronal cells in vivo. When cultured ex vivo, neural stem cells can be induced to proliferate and differentiate into different types of neurons and glial cells. When transplanted into the brain, neural stem cells can engraft and generate neural cells and glial cells.

Mesenchymal stem cells (MSC), originally derived from the embryonal mesoderm and isolated from adult bone marrow, can differentiate to form muscle, bone, cartilage, fat, marrow stroma, and tendon. Mesoderm also differentiates into visceral mesoderm which can give rise to cardiac muscle, smooth muscle, or blood islands consisting of endothelium and hematopoietic progenitor cells. All of the many mesenchymal stem cells that have been described have demonstrated limited differentiation to cells generally considered to be of mesenchymal origin. To date, the best characterized mesenchymal stem cell reported is the cell isolated by Pittenger, et al. (Science (1999) 284: 143-147 and U.S. Pat. No. 5,827,740 (SH2$^+$ SH4$^+$ CD29$^+$ CD44$^+$ CD71$^+$ CD90$^+$ CD106$^+$ CD120a$^+$ CD124$^+$ CD14$^-$ CD34$^-$ CD45$^-$)). This cell is apparently limited in differentiation potential to cells of the mesenchymal lineage.

There is a need, therefore, for a non-embryonic stem cell that has the capacity to form differentiated cells of more than one embryonic lineage.

Myocardial Infarct (MI)

Myocardial infarction (MI) is characterized by the death of myocytes, coagulative necrosis, myocytolysis, contraction band necrosis, or apoptosis, resulting from a critical imbalance between the oxygen supply and demand of the myocardium. The most common cause of MI is coronary artery thrombosis following the rupture of atheromatous plaques. Though once strictly defined as a lack of blood flow, the modern definition of ischemia emphasizes the imbalance between oxygen supply and demand as well as the inadequate removal of metabolic waste products.

Impaired oxygen delivery results in a reduction in oxidative phosphorylation that causes anaerobic glycolysis. This produces excess lactate that accumulates in the myocardium. Impaired ATP production and acidosis results in a decline in myocardial contractility. Similarly, ischemia reperfusion injury, without total occlusion, can also cause cardiac damage.

The exposure of the contents of the plaque to the basement membrane following plaque rupture ultimately results in vessel blockage culminating from a series of events including platelet aggregation, thrombus formation, fibrin accumulation, and vasospasm. Total occlusion of the vessel for more than 4-6 hours results in irreversible myocardial necrosis. Ultimately, death and morbidity from myocardial infarction is the result of fatal dysrhythmia or progressive heart failure. Progressive heart failure is chiefly the result of insufficient muscle mass (deficiency in muscle cells) or improper function of the heart muscle, which can be caused by various conditions including, but not limited to, hypertension. Progressive heart failure is, therefore, the focus of cell-based therapy.

All current strategies for the treatment of myocardial infarction focus on limiting myocyte death. Annually in the United States, 500,000 patients undergo angioplasty with stent placement. 400,000 will undergo coronary artery bypass, while an unknown additional number of patients will be treated by thrombolytic therapy.

One approach, known as cellular cardiomyoplasty, has received recent attention and focuses on repopulation and engraftment of the injured myocardium by transplantation of healthy cells (Reffelmann, T. and Kloner, R. A. (2003) *Cardiovasc Res.* 58(2): 358-68). Many cell types that might replace necrotic tissue and minimize regional scarring have been considered. Cells that have already committed to a specific lineage, such as satellite cells, cardiomyocytes, primary myocardial cell cultures, fibroblasts, and skeletal myoblasts, have been readily used in cellular cardiomyoplasty with limited success in restoring damaged tissue and improving cardiac function (Menasche, P. (2003) *Cardiovasc Res.* 58(2): 351-7; Etzion, S. et al (2001) *J Mol Cell Cardiol.* 33(7): 1321-30; Sakai, T. et al (1999) *J. Thorac. Cardiovasc. Surg.* 118(4): 715-24).

Cardiogenic progenitors are precursor cells that have committed to the cardiac lineage, but have not differentiated into cardiac muscle. Cardiomyocytes are the cells that comprise the heart. They are also known as cardiac muscle cells. Use of cardiomyocytes in the repair of cardiac tissue has been proposed. However, this approach is hindered by an inability to obtain sufficient quantities of cardiomyocytes for the repair of large areas of infarcted myocardium. Doubt has also been cast over the incorporation and tissue-specific function of intra-cardiac grafts derived from cardiomyocytes, even when they are harvested from embryonic sources (Etzion, S. et al (2001) *J. Mol. Cell. Cardiol.* 33(7): 1321-30). Intra-cardiac grafts using this cell type can be successfully grafted and are able to survive in the myocardium after permanent coronary artery occlusion and extensive infarction. However, engrafted rat embryonic cardiomyocytes attenuate, but do not fully reverse, left ventricular dilatation and prevent wall thinning. While survival was improved during 8 weeks of follow-up, the implanted cells did not develop into fully differentiated myocardium. Surprisingly, they remained isolated from the host myocardium by scar tissue and did not improve systolic function over time (Etzion, S. et al (2001) *J. Mol. Cell. Cardiol.* 33(7): 1321-30).

Congestive Heart Failure

Congestive heart failure (CHF) is a clinical condition in which a primary or secondary circulatory system disease causes abnormal cardiac pressure or performance characteristics that lead to pulmonary congestion (Zhang, J. and Narula, J. (2004) *Surg Clin N Am* 84:223-242). CHF is a chronic condition that results when the heart muscle is unable to pump blood as efficiently as is needed to maintain physiological homeostasis. Although common causes of CHF include hypertension, anemia and cardiomyopathy, CHF is most often caused by myocardial infarction (Lee, Michael, et al (2004) *Reviews in Cardiovascular Medicine*, 5: 82-94). Currently, nearly 550,000 new cases of heart failure are now diagnosed each year.

CHF occurs when cardiac dysfunction prevents adequate perfusion of peripheral tissues. Inadequate perfusion leads to stimulation of compensatory mechanisms that then cause many of the clinical signs and symptoms of the condition. In patients with CHF, neurohumoral compensatory mechanisms are activated. Chronic stimulation by these agents increases cardiac afterload and preload, further worsening ventricular function.

Small molecule therapeutics are being tested with the aim to disrupt these compensatory systems. However, no pharmacological intervention improves the underlying pathophysiology of CHF.

Surgical intervention to treat CHF is also limited. Cardiac transplantation is the mainstay of treatment for patients with end-stage cardiomyopathies, such as CHF, but is limited by the scarcity of donor organs and complications, such as graft rejection and allograft coronary vasculopathy (Fedak, P. et al (2003) *Seminars in Thoracic and Cardiovascular Surgery*, 15: 277-286).

Recent studies challenge the traditional dogma that the heart is a terminally differentiated post-mitotic organ incapable of self-renewal. This opens the door to the possibility of delivering cells to treat CHF. It would be desirable to repopulate the injured cells with stem cells to regenerate cardiomyocytes and blood vessels, reverse ventricular remodeling, or reduce apoptosis of existing cells. Both myogenesis and angiogenesis may be required to restore cardiac function in patients with transmural scar tissue. Thus, cells that are capable of inducing angiogenesis and forming muscle-like cells and endothelial cells may be useful to reverse cardiac dysfunction in patients with CHF.

Clinical Experience with Stem Cells to Treat Cardiovascular Disease

Given the feasibility of the procedure, autologous skeletal muscle cell transplantation has been used clinically (Menasche P et al (2001) *Lancet* 357:279-280). Autologous skeletal myoblasts were directly injected into nonviable regions of the heart at the time of coronary bypass grafting or LVAD insertion. They formed viable grafts (Pagani F et al (2002) *Circulation* 106:11463 (abstract)). Patients reported improved symptoms and global heart functions. There was also evidence of viability in the dead region after clinical cell transplantation.

Both autologous bone marrow cells and myoblasts have been used clinically in humans in a CHF setting. Strauer and co-workers transplanted autologous mononuclear bone marrow cells in patients with acute myocardial infarction (Trauer et al (2002) *Circulation* 106: 1913-1918). Regions of cell delivery demonstrated increased perfusion, viability, and wall motion, demonstrating improved myogenesis and angiogenesis.

Bone marrow cell-derived progenitor cells and circulating progenitor cells have also been tested (Assmus et al (2002)

*Circulation* 106:3009-3017). Treatment was associated with improved regional and global heart function, improved viability in the infarct area, and reduced left ventricular end-systolic volumes.

Human ES cells have been demonstrated to differentiate into myocytes with many of the functional characteristics of cardiomyocytes (Cai, J. (2002) *Neuromolecular Med,* 2(3): 233-49). There are, however, safety concerns regarding therapeutic use because ES cells cause the formation of teratomas when administered to animals.

Adult stem cells that are dispersed throughout normal adults and can be isolated from a number of tissue sources, including organs, bone marrow and blood. They are free from many of the ethical and safety issues associated with ES cells (Cai, J. (2002) *Neuromolecular Med,* 2(3): 233-49) and have not been linked to the growth of teratomas or cancerous tumors. However, adult stem cells have shown limitations in their potential for therapeutic applications in that their differentiation potential generally appears to be restricted to narrowly-defined cell lineages or tissues, typically reflecting the tissue or organ from which the cells were isolated (Raff, M. (2003) *Annu Rev Cell Dev Biol* 19: 1-22; Verfaillie, C. M. (2002) *Trends Cell Biol,* 12(11): 502-8).

Hematopoietic stem cells (HSC) have been utilized therapeutically for several decades in immune reconstitution settings.

In summary, loss of function and/or cell mass in cardiac muscle can arise, for example, by physical damage or disease-related damage (e.g., genetic or acquired disease). Stem cell technology has made cellular myoplasty a realistic treatment for restoring or enhancing cardiac muscle function or cell mass. Tissue-specific stem cells and embryonic stem cells provide limited results.

SUMMARY OF THE INVENTION

A population of non-embryonic stem cells, designated by the inventors as multipotent adult progenitor cells (MAPCs), can effectively restore or enhance cardiac muscle function in damaged tissues.

MAPC is an acronym for "multipotent adult progenitor cell" (non-ES, non-EG, non-germ) that has the capacity to differentiate into cells of more than one embryonic lineage. It can form cell types of all three primitive germ layers (ectoderm, mesoderm, and endoderm). The inventors were the first to discover the existence of such a cell. Genes that are found in ES cells were also found in the MAPC (e.g., telomerase, Oct 3/4, rex-1, rox-1, sox-2). Thus the inventors identified a class of new multipotent stem cells from non-embryonic and non-germ tissue. Telomerase or Oct 3/4 can be recognized as genes that are primary products for the undifferentiated state. Telomerase, as discussed herein, is necessary for self-renewal. Oct 3/4 (Oct 3A in humans) appears to be specific for ES and germ cells.

Biologically and antigenically distinct from MSC, MAPC represents a more primitive progenitor cell population than MSC and demonstrates differentiation capability encompassing the epithelial, endothelial, neural, myogenic, hematopoeitic, osteogenic, hepatogenic, chondrogenic and adipogenic lineages (Verfaillie, C. M. (2002) *Trends Cell Biol.* 12(11): 502-8, Jahagirdar, B. N., et al. (2001) *Exp Hematol,* 29(5): 543-56). MAPCs thus represent a new class of non-embryonic stem cell that emulates the broad biological plasticity characteristic of ES cells, while maintaining the other characteristics that make non-embryonic stem cells appealing. For example, MAPCs are capable of indefinite culture without loss of their differentiation potential and show efficient, long term, engraftment and differentiation along multiple developmental lineages in NOD-SCID mice without evidence of teratoma formation (Reyes, M. and C. M. Verfaillie (2001) *Ann N Y Acad Sci,* 938: 231-3).

MAPCs were initially isolated from bone marrow but subsequently have been established from other tissues, including brain, muscle, and cord blood (Jiang, Y., et al. (2002) *Exp Hematol,* 30(8): 896-904). Adherent cells from bone tissue are enriched in media containing low serum (2%), dexamethasone, EGF, PDGF, and other additives, and grown to high population doublings. At early culture points more heterogeneity is detected in the population. Then, many adherent stromal cells undergo replicative senescence around cell doubling 30 and a more homogenous population of cells continues to expand and maintains long telomeres.

The present invention, therefore, provides a method of repairing damaged heart tissue in a subject in need of such repair by contacting an effective amount of multipotent adult stem cells with the damaged tissue of said subject. The cells can be autologous, allogenic or xenogenic. In one embodiment the cells are allogeneic, so that cell banks are available for rapid response.

The invention further provides genetically engineered MAPCs to selectively express an endogenous gene or a transgene to treat tissue damage.

MAPC or progeny can be used to treat cardiac diseases including, but not limited to, myocarditis, cardiomyopathy, heart failure, damage caused by heart attacks, hypertension, atherosclerosis, and heart valve dysfunction. Progeny can include cardiomyocytes that repopulate the injured tissue or endothelial cells that provide neo-vascularization to the tissue.

The present invention relates to methods of improving function and/or cell mass in cardiac muscle tissue by administering MAPCs. MAPCs can engraft into the tissue to be treated in both healthy and damaged sites.

In another embodiment, the present invention comprises methods of providing cardiac muscle cells in a subject comprising administering an amount of MAPCs to the subject effective to generate new cardiac muscle cells.

In another embodiment, the present invention comprises methods of increasing cardiac muscle mass in a subject comprising providing an amount of MAPCs to generate new cardiac muscle.

The methods can further comprise preliminary measures of isolating and expanding a population of MAPCs.

In preferred embodiments, engraftment of MAPCs is in cardiac muscle in acute myocardial infarction.

In yet another embodiment, the present invention comprises administration of MAPCs to a subject in need thereof in the presence of cytokines to enhance homing of MAPCs to damaged or abnormal cardiac muscle, and to enhance differentiation of MAPCs or other progenitors into cells of the myogenic lineage (e.g., cardiomyocytes, myocytes, myoblasts and terminally-differentiated muscle cells).

In another aspect, the present invention comprises methods of increasing cardiac muscle in a subject comprising providing a suitable amount of MAPCs to existing cardiac muscle and generating new cardiac muscle.

In yet another aspect, the present invention comprises methods of increasing cardiac muscle function in a subject comprising providing MAPCs to existing cardiac muscle in an amount sufficient to increase cardiac muscle function.

Cells integrating within, and therefore contributing to, the generation of new muscle can include endogenous stem or progenitor cells (e.g., MAPCs), recruited stem or progenitor cells, exogenous MAPCs and combinations thereof.

In one embodiment, the present invention comprises methods of improving cardiac function in a subject comprising administering an amount of MAPCs to the subject effective to improve cardiac function.

Evaluation of cardiac function can be monitored using various well-known imaging techniques such as myocardial perfusion imaging, gated cardiac blood-pool imaging, first-pass ventriculography, right-to-left shunt detection, positron emission tomography, single photon emission computed tomography, magnetic resonance imaging, harmonic phase magnetic resonance imaging, echocardiography, and myocardial perfusion reserve imaging.

Administered MAPCs may contribute to generation of new tissue by differentiating into muscle cells in vivo. Alternatively, or in addition, administered MAPCs may contribute to generation of new tissue by secreting cellular factors that aid in homing and recruitment of endogenous MAPCs or other stem cells, such as cardiac, hematopoietic or mesenchymal stem cells, or other more differentiated cells, such as skeletal myoblasts, cardiac myoblasts and myocytes. Alternatively, or in addition, MAPCs may secrete factors that act on endogenous stem or progenitor cells in the target tissue causing them to differentiate in the target site, thereby enhancing function. Further, MAPCs may secrete factors that act on stem, progenitor, or differentiated cells in the target tissue, causing them to divide. Further, MAPCs may provide for angiogenesis or reduce or prevent apoptosis.

In one embodiment, MAPC-based therapies can be used to treat damage resulting from disease states including congestive heart failure, coronary artery disease, myocardial infarction, myocardial ischemia, effects of atherosclerosis or hypertension, cardiomyopathy, cardiac arrhythmias, muscle degeneration, infective myocarditis, drug- and toxin-induced muscle abnormalities, hypersensitivity myocarditis, autoimmune endocarditis, and congenital heart disease.

MAPCs can be administered to a subject by localized or systemic injection. A variety of methods known in the art include, but are not limited to, surgical intramyocardial injection, transendocardial injection, intracoronary injection, transvascular injection, intramuscular injection, and intravenous injection. MAPCs may be administered within or in proximity to the site requiring new muscle cells, or enhanced function. Alternatively, they can be administered at a remote location.

The cells can be introduced into the body of the subject in conjunction with a suitable matrix implant. The matrix implant may provide additional genetic material, cytokines, growth factors, or other factors to promote growth and differentiation of the cells. The cells can be encapsulated prior to introduction into the body of the subject, such as within a polymer capsule.

Other aspects of the invention are described in or are obvious from the following disclosure, and are within the ambit of the invention.

BRIEF DESCRIPTIONS OF THE DRAWINGS

FIG. 1. Transcriptional profiling studies were performed to generate gene and surface receptor-based markers that distinguish between multipotent stem cells of the invention and more lineage-committed stem and progenitor cells. The experiments have resulted in a panel of 75 markers having 10-fold different expression between MSC cultures and the MAPCs.

Figure 2:
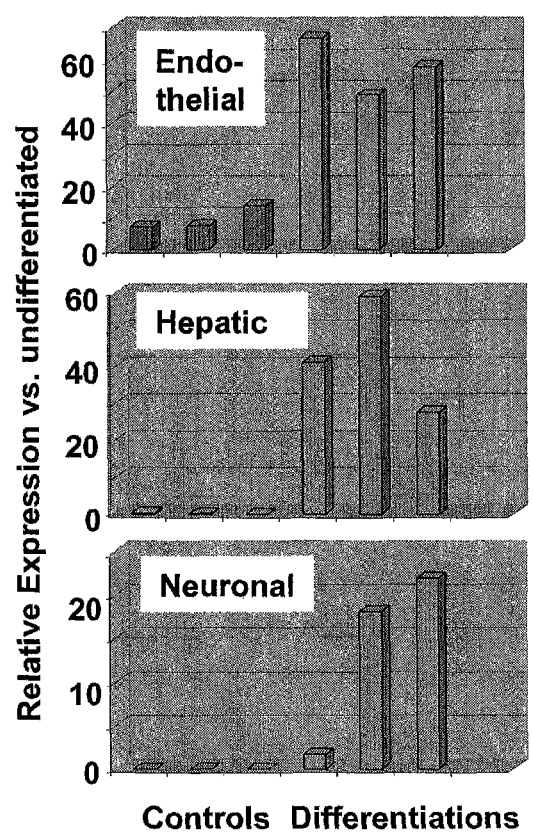

FIG. 2. Tri-lineage differentiation of GFP-labeled rat MAPC. For endothelial differentiation, MAPCs were cultured on fibronectin-coated plates in the presence of vascular endothelial growth factor (VEGF)-B. For hepatocyte differentiation, cells were grown on matrigel-coated plates and treated with fibroblast growth factor-4 (FGF-4) and hepatocyte growth factor (HGF). Neuronal differentiation was induced by sequential treatment with basic-FGF (bFGF), with both FGF-8 and Sonic Hedgehog (SHH), and with brain-derived neurotrophic factor (BDNF). After two weeks mRNA was extracted from cells and applied to qPCR analysis using primers specific for detection of various lineage markers. In all assays, cells cultured in the absence of lineage-inducing cytokines served as controls. The expression levels of lineage markers were first normalized to an internal control gene (GAPDH) which expression levels are unaffected during differentiation. Differentiation success was then assessed by calculation of the relative expression in the differentiated or the control cells compared to the levels in the parental rat line, using an increase of more than 5-fold in the relative expression as a cut-off for successful differentiation. Differentiated rat MAPCs displayed significant expression of the endothelial markers, von Willebrand factor and PECAM-1 (top panel), the hepatic markers albumin, cytokeratin-18 and HNF-1a (middle panel), and the neuronal/astrocyte markers GFAP, nestin and NF-200 (bottom panel).

Figure 3:
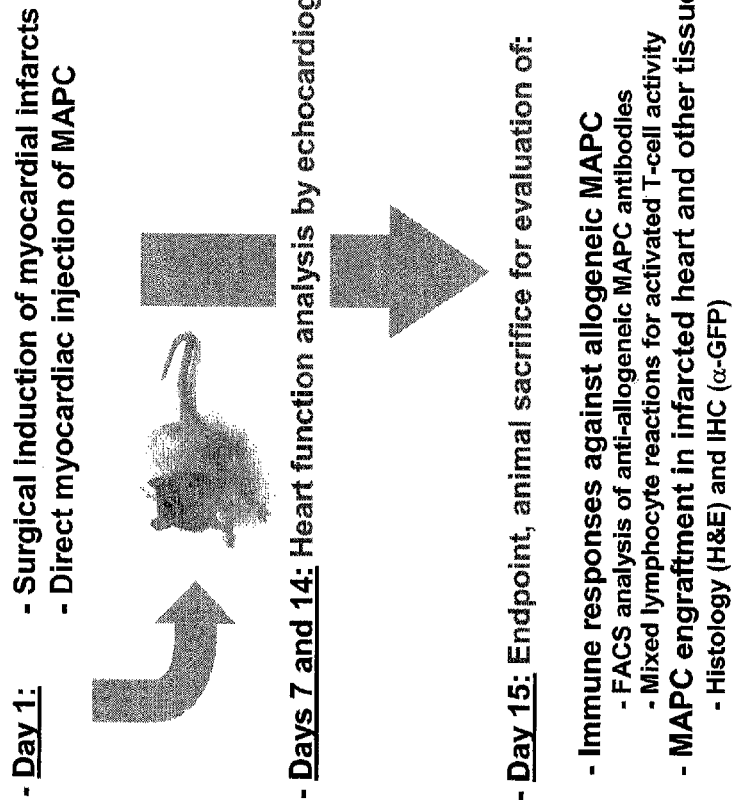

FIG. 3. Schematic of the timeline following surgical induction of myocardial infarction and direct myocardiac injection of the MAPC. The timeline shows heart function analysis by echocardiography and the end point involving animal sacrifice to evaluate immune responses and stem cell engraftment. H&E: hematoxylin/eosin stain; α-GFP: detection by anti-GFP antibody.

Figure 4:
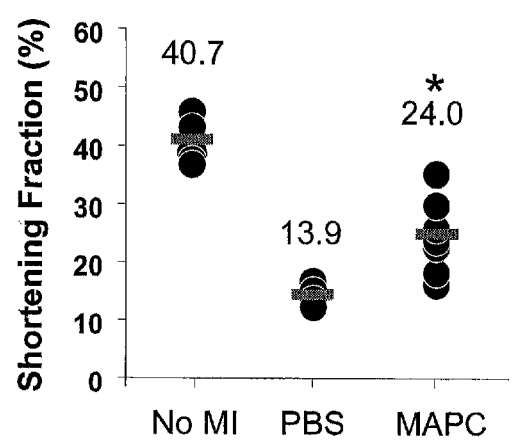

FIG. 4. Assessment of the shortening fraction two weeks after MI induction and MAPC injection. Lewis rats received either no MI surgery (no MI), or received LAD ligation followed by myocardial administration of PBS (PBS) or 2 million MAPC in 5 separate injections of 400,000 cells in the infarct border zone (MAPC). After two weeks animals were subjected to echocardiography for measurement of the shortening fraction. For each animal the left ventricular end diastolic dimension (LVEDD) and the left ventricular end systolic dimension (LVESD) were measured five separate times and the mean values were used to calculate the shortening fraction (SF) according to the following formula: SF=(LVEDD-LVESD)/LVEDD*100. The asterisk in the figure indicates a significant difference between the MAPC and the PBS control group (Dunn's test, nonparametric multiple comparisons).

Figure 5:
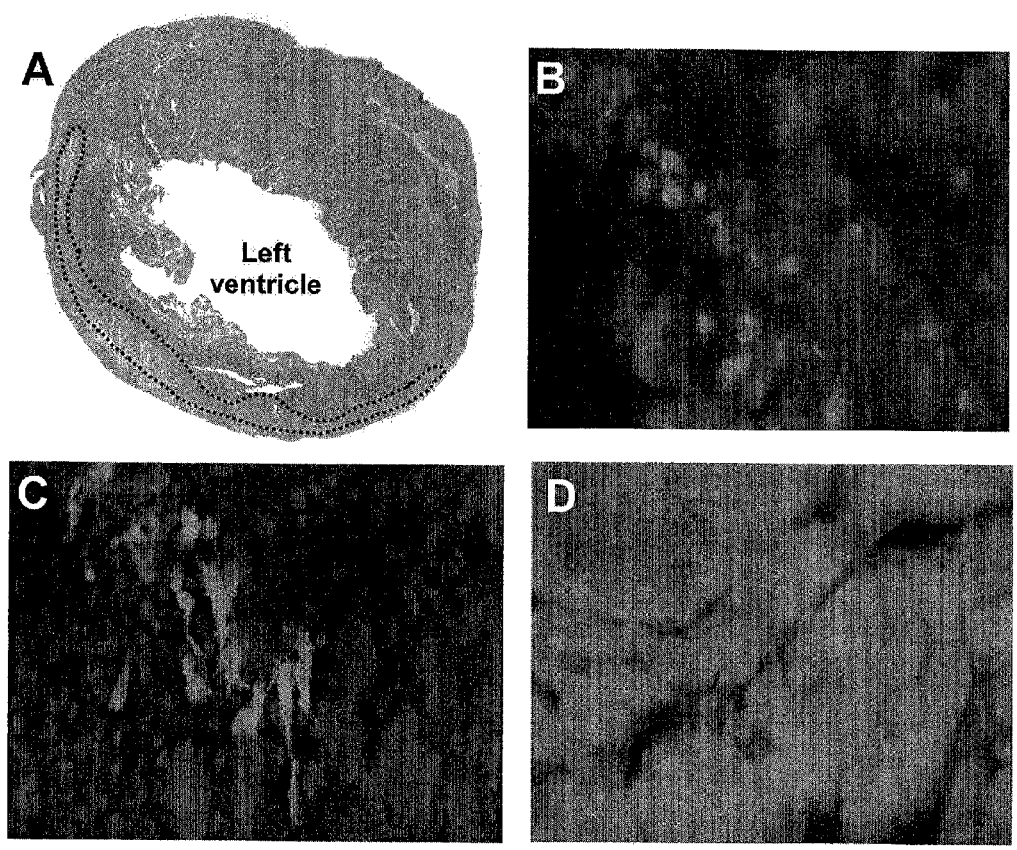

FIG. 5. Morphological analysis of MI induction and MAPC engraftment. Two weeks after MI surgery and MAPC injection (see FIG. 3), animals were sacrificed and the hearts were harvested. (A) Semi-thin cross-sections of plastic embedded tissue were stained with hematoxylin/eosin for gross morphological evaluation. The infarcted region in the left ventricular wall is highlighted by the dotted line. (B, C and D) Sections were labeled with primary goat anti-GFP antibody, followed by secondary Alexa-fluor-488 conjugated anti-goat IgG antibody and DAPI staining Nuclei are blue and GFP positive cells are green. Autofluorescent signals in the tissue are caused by lipofuscins (pink) and myofbrils (yellow). Orange signal in (D) is caused by erythrocytes. GFP positive cells are observed the infarcted heart tissue (A), in the border zone (B) and within areas containing healthy myofibrils. Note the extension and re-arrangement of GFP positive MAPCs within the host cells in the tissue, and the apparent lack of accumulation of infiltrating inflammatory cells.

Figure 6:
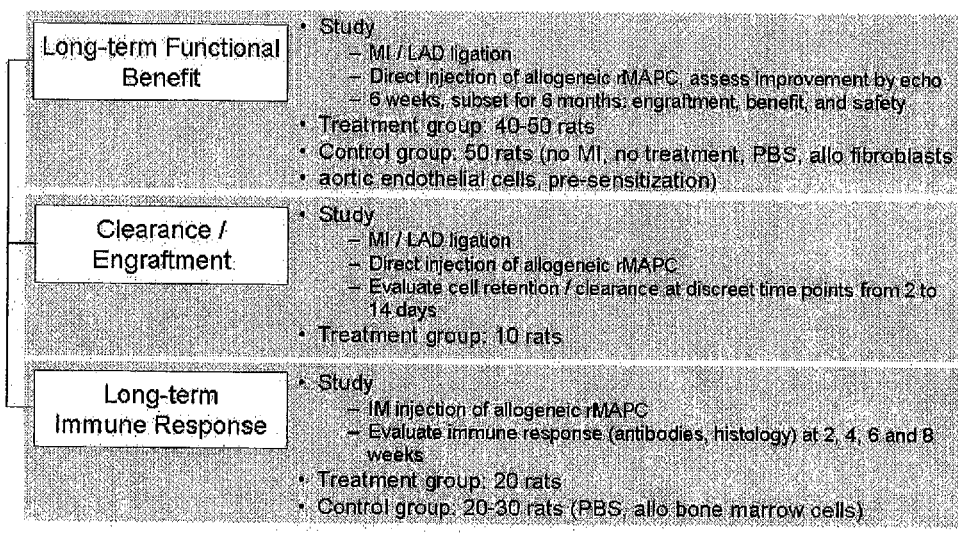

FIG. 6. Schematic of a phase II study showing long-term functional benefit, clearance and engraftment, and long-term immune response.

Figure 7:
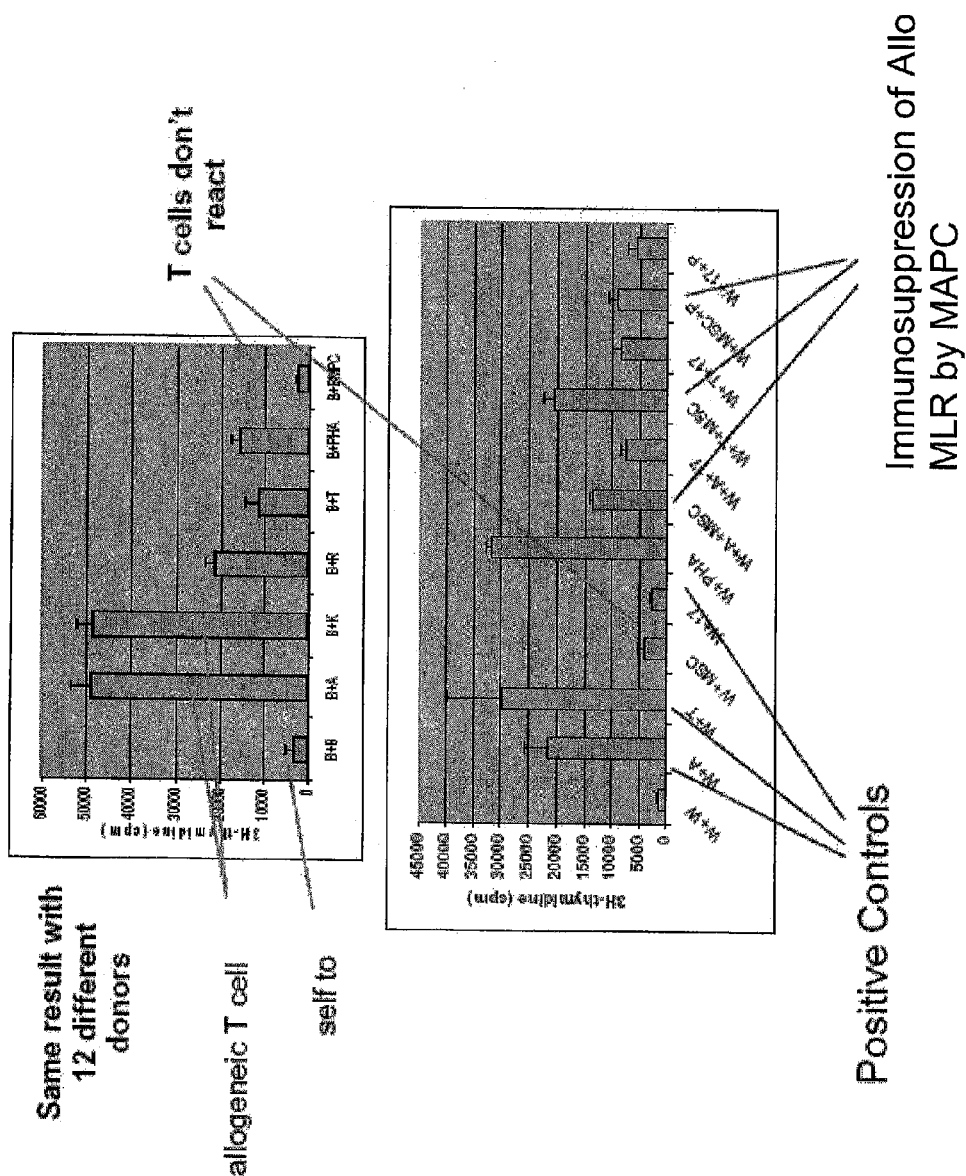

FIG. 7. Low immunogenicity (top panel) and immunosuppression (bottom panel) by MAPC as shown by mixed lymphocyte reaction assay (MLR). Top: B+B=donor B+donor B; B+A=donor B+donor A; B+K=donor B+donor K; B+R=donor B+donor R; B+T=donor B+donor T; B+BMPC=donor B+MAPC. The same result was achieved with twelve different donors. Bottom: donor W+donor W; donor W+donor A; donor W+donor T; donor W+MSC; donor W+MAPC (17); donor W+donor A+MSC; donor W+donor A+MAPC (17); donor W+donor T+MSC; donor W+donor T+MAPC (17); donor W+donor P+MSC; donor W+donor P+MAPC (17). This figure shows that MAPC have immunosuppressive properties that are characteristic of MSC. They, therefore, provide the potential for in vivo treatment with allogeneic MAPC.

DETAILED DESCRIPTION OF THE INVENTION

MAPC have the ability to regenerate all primitive germ layers (endodermal, mesodermal, and ectodermal) in vitro and in vivo. In this context they are equivalent to embryonal stem cells, and distinct from mesenchymal stem cells, which are also isolated from bone marrow. The biological potency of these cells has been proven in various animal models, including mouse, rat, and xenogeneic engraftment of human stem cells in rats or NOD/SCID mice (Reyes, M. and C. M. Verfaillie (2001) Ann N Y Acad Sci. 938: 231-3; Jiang, Y. et al. (2002) Exp Hematol. 30(8): 896-904). Clonal potency of this cell population has been shown. Single genetically marked MAPC were injected into mouse blastocysts, blastocysts implanted, and embryos developed to term (Jiang, Y. et al. (2002) Nature 418(6893): 41-9.). Post-natal analysis in highly chimeric animals showed reconstitution of all tissues and organs, including liver. Dual staining experiments demonstrated that gene-marked stem cells contributed to a significant percentage of apparently functional cardiomyocytes in these animals. These animals did not show any heart abnormalities or irregularities in either embryological or adult state. No abnormalities or organ dysfunction were observed in any of these animals.

Definitions

As used herein, the terms below are defined by the following meanings.

"MAPC" is an acronym for "multipotent adult progenitor cell". It refers to a non-embryonic stem cell that can give rise to cell types of more than one embryonic lineage. It can form cell lineages of all three germ layers (i.e., endoderm, mesoderm and ectoderm) upon differentiation. Like embryonic stem cells, human MAPCs express telomerase, Oct 3/4 (i.e., Oct 3A), rex-1, rox-1 and sox-2 and telomerase. MAPC may express SSEA-4, and nanog. The term "adult" in MAPC is non-restrictive. It refers to a non-embryonic somatic cell.

MAPCs constitutively express Oct 3/4 and high levels of telomerase (Jiang, Y. et al (2002) Nature 418:41-49; Exp Hematol. 30(8):896). MAPCs derived from human, mouse, rat or other mammals appear to be the only normal, non-malignant, somatic cell (i.e., non-germ cell) known to date to express very high levels of telomerase even in late passage cells. The telomeres are extended in MAPCs and they are karyotypically normal. Because MAPCs injected into a mammal can migrate to and assimilate within multiple organs, MAPCs are self-renewing stem cells. As such, they have utility in the repopulation of organs, either in a self-renewing state or in a differentiated state compatible with the organ of interest. They have the capacity to replace cell types that could have been damaged, died, or otherwise might have an abnormal function because of genetic or acquired disease. Or, as discussed below, they may contribute to the preservation of healthy cells or production of new cells in a tissue.

"Multipotent", with respect to MAPC, refers to the ability to give rise to cell types of more than one embryonic lineage. MAPC can form cell lineages of all three primitive germ layers (i.e., endoderm, mesoderm and ectoderm) upon differentiation.

"Expansion" refers to the propagation of a cell or cells without differentiation.

"Progenitor cells" are cells produced during differentiation of a stem cell that have some, but not all, of the characteristics of their terminally-differentiated progeny. Defined progenitor cells, such as "cardiac progenitor cells," are committed to a lineage, but not to a specific or terminally-differentiated cell type. The term "progenitor" as used in the acronym "MAPC" does not limit these cells to a particular lineage.

The term "isolated" refers to a cell or cells not associated with one or more cells or one or more cellular components that are associated with the cell or cells in vivo. An "enriched population" means a relative increase in numbers of MAPC relative to one or more non-MAPC cell types in vivo or in primary culture.

"Cardiomyocyte" refers to cells that comprise the heart and are also known as cardiac muscle cells. A "myoblast" is a mononucleated, undifferentiated muscle precursor cell.

"Cardiogenic progenitors" are precursor cells that have committed to the cardiac lineage, but have not differentiated into cardiac muscle.

"Self-renewal" refers to the ability to produce replicate daughter stem cells having differentiation potential that is identical to those from which they arose. A similar term used in this context is "proliferation."

"Striated muscle" refers to muscle having actin and myosin filaments aligned in orderly arrays to form a series of contractile units which give the cells a striated appearance. Types of striated muscle include skeletal and cardiac muscle.

"Engraft" refers to the process of cellular contact and incorporation into an existing tissue of interest in vivo.

"Persistence" refers to the ability of cells to resist rejection and remain and/or increase in number over time (e.g., days, weeks, months, years) in vivo.

The term "cytokines" means cellular factors that induce or enhance cellular movement, such as homing of MAPCs or other stem cells, progenitor cells or differentiated cells such as skeletal myoblasts, cardiac myoblasts, myocytes, and the like. Cytokines may also stimulate such cells to divide.

The phrase "differentiation factors" means cellular factors, preferably growth factors or angiogenic factors, that induce lineage commitment.

A "Subject" is a vertebrate, preferably a mammal, more preferably a human. Mammals include, but are not limited to, humans, farm animals, sport animals, and pets. Subjects in need of treatment by methods of the present invention include those suffering from a loss of function in striated muscle as a result of physical or disease-related damage. Disease states characterized by loss of striated muscle mass and/or function, and that benefit from methods of the present invention include, but are not limited to, congestive heart failure, coronary artery disease, myocardial infarction, myocardial ischemia, atherosclerosis, cardiomyopathy, cardiac arrhythmias, muscular dystrophies, muscle mass abnormalities, muscle degeneration, myasthenia gravis, infective myocarditis, drug- and toxin-induced muscle abnormalities, hypersensitivity myocarditis, autoimmune endocarditis, and congenital heart disease.

As used herein, "treat", "treating", or "treatment" includes treating, preventing, ameliorating, inhibiting or removing an injury or disease-related condition and/or symptom of an injury or disease-related condition.

An "effective amount" generally means an amount which provides the desired local or systemic effect, such as enhanced performance. For example, an effective dose is an amount sufficient to effect a beneficial or desired clinical result. The dose can be administered in one or more administrations and can include any preselected amount of cells. The precise determination of what would be considered an effective dose may be based on factors individual to each subject, including size, age, injury and/or disease or injury being treated and amount of time since the injury occurred or the disease began. One skilled in the art, particularly a physician, would be able to determine the number of cells that would constitute an effective dose.

"Co-administer" can include simultaneous or sequential administration of two or more agents.

Administered MAPCs may contribute to generation of new tissue by differentiating into specific cells, such as cardiomyocytes, in vivo. Alternatively, or in addition, administered MAPCs may contribute to generation of new tissue by secreting cellular factors that aid in homing and recruitment of endogenous MAPCs or other stem cells, or other more differentiated cells, such as cardiomyocytes. Alternatively, or in addition, MAPCs may secrete factors that act on endogenous stem or progenitor cells in the target tissue causing them to differentiate in the target site, thereby enhancing function. Further, MAPCs may secrete factors that act on stem, progenitor, or differentiated cells in the target tissue, causing them to divide. Thus, MAPCs may provide benefit through trophic influences. Examples of trophic influences include, but are not limited to, limiting inflammatory damage, limiting vascular permeability, improving cell survival and homing of repair cells to sites of damage. Additionally, MAPCs may also provide benefit by increasing capillary density and stimulating angiogenesis. This may be achieved by production of angiogenic factors, such as VEGF, or by differentiation of the MAPCs and inclusion in new vessel tissue, or both. Therapeutic benefit may be achieved by a combination of the above pathways.

The terms "comprises", "comprising", and the like can have the meaning ascribed to them in U.S. Patent Law and can mean "includes", "including" and the like. As used herein, "including" or "includes" or the like means including, without limitation.

Administration of MAPCs

MAPCs can be administered to a subject by a variety of methods known in the art. Preferably, administration is through injection, including but not limited to, surgical intramyocardial injection, transendocardial injection, intracoronary injection, transvascular injection, intramuscular injection, and intravenous injection.

Surgical myocardial injection is an invasive approach that may be particularly suitable to patients who are undergoing concurrent surgical procedures. The injection process can be performed under direct visualization, such as by using a small gauge needle, thereby allowing evaluation by direct inspection of potential target zones. Not all areas of the myocardium can be readily accessed with this approach. Usually, multiple injections are made in a particular region, usually around a border zone. Direct injection can be performed when the patient is connected to a heart lung machine, in which case the cells can be very precisely administered.

Transendocardial injection primarily involves a catheter system known as NOGA. The injection catheter incorporates the mapping capabilities of the system. This provides a means by which tissues with different degrees of viability and ischemia can be mapped in detail, allowing therapy to be precisely targeted (e.g., at the border zone of an infarct). NOGA catheters can be used alongside detection techniques such as magnetic resonance imaging (MRI), echocardiogram (EKG), or computed tomographic techniques such as positron emission tomography (PET) or single photon emission computed tomography (SPECT).

Intracoronary injection is particularly well suited for delivery of cells to a specific coronary territory. It is less complex than transendocardial delivery, and because of the segmental nature of coronary artery disease, may be more practical than other techniques. Where retention of cells in the target area is at issue, this technique is especially suited for treating relatively intense ischemia. The quantity of cells and time of infusion can be carefully monitored to avoid coronary flow impairment and myocardial cell necrosis.

Intravenous injection is the simplest method of cell administration, although a greater degree of dependence on homing of the stem cells is required for them to reach the tissue of interest (e.g., myocardium). Carefully controlled dosing, which is readily determined by one skilled in the art, enhances this method of administration.

With respect to timing of administration for myocardial infarction, the preferred embodiment would likely be a few days after the event or at least after the patient is sufficiently stabilized. Current clinical trials in the art administer cell therapy about four days after the event (see, for example, *Circulation* (2002)106:3009-3017).

For congestive heart failure the preferred embodiment would be transendocardial via catheter or direct injection. Also, for congestive heart failure, preferred embodiments encompass bioengineered patches of cells contained within biodegradable matrices. For coronary artery disease the preferred embodiment would be intracoronary in order to stimulate neovascularization and also to potentially treat underlying atherosclerosis.

Certain cytokines can alter or affect the migration of MAPCs or their differentiated counterparts to the site of damaged muscle tissue. "Homing" of stem cells to the injured muscle tissues would concentrate the implanted cells in an environment favorable to their growth and function. In more acutely ischemic situations, the stem cells can be administered either peripherally or locally through the circulatory system. When the homing signals may be less intense, as may be the case for chronic ischemic or nonischemic cardiomyopathies, injection of the cells directly into the cardiac muscle may produce a more favorable outcome. Pre-treatment of a patient with cytokine(s) to promote homing is another alternative contemplated in the methods of the present invention.

Cytokines include, but are not limited to, stromal cell derived factor-1 (SDF-1), stem cell factor (SCF), angiopoietin-1, placenta-derived growth factor (PIGF) and granulocyte-colony stimulating factor (G-CSF). Cytokines also include any which promote the expression of endothelial adhesion molecules, such as ICAMs, VCAMs, and others, which facilitate the homing process.

Differentiation of MAPCs to a phenotype characteristic of muscular tissues can be enhanced when differentiation factors are employed. Differentiation factors promoting muscle formation include, but are not limited to vascular endothelial growth factor (VEGF), fibroblast growth factors (e.g., FGF4, FGF8, bFGF) Wnt11, DKK1, ascorbic acid, isoproterenol and endothelin.

Viability of newly forming tissues can be enhanced by angiogenesis. Differentiation factors promoting angiogenesis include, but are not limited to, VEGF, aFGF, angiogenin, angiotensin-1 and -2, betacellulin, bFGF, Factor X and Xa, HB-EGF, PDGF, angiomodulin, angiotropin, angiopoetin-1, prostaglandin E1 and E2, steroids, heparin, 1-butyryl-glycerol and nicotinic amide.

Factors that decrease apoptosis can also promote the formation of new striated muscle. Factors that decrease apoptosis include, but are not limited to, β-blockers, angiotensin-converting enzyme inhibitors (ACE inhibitors), AKT, HIF, carvedilol, angiotensin II type 1 receptor antagonists, caspase inhibitors, cariporide, and eniporide.

Exogenous factors (e.g., cytokines, differentiation factors and anti-apoptosis factors) can be administered prior to, after or concomitantly with MAPCs. For example, a form of concomitant administration would comprise combining a factor of interest in the MAPC suspension media prior to administration. Administrations are variable and may include an initial administration followed by subsequent administrations, ascertained by the skilled artisan from this disclosure, and the knowledge in the art.

A method to potentially increase cell survival is to incorporate MAPCs or other cells of interest into a biopolymer or synthetic polymer. Depending on the patient's condition, the site of injection might prove inhospitable for cell seeding and growth because of scarring or other impediments. Examples of biopolymer include, but are not limited to, cells mixed with fibronectin, fibin, fibrinogen, thrombin, collagen, and proteoglycans. This could be constructed with or without included cytokines or differentiation factors. Additionally, these could be in suspension but residence time at sites subjected to flow would be nominal. Another alternative is a three-dimensional gel with cells entrapped within the interstices of the cell biopolymer admixture. Again differentiation factors or cytokines could be included within the cells. These could be deployed by injection via various routes described herein, via cardiac catheters or other surgical procedures.

In current human studies of autologous mononuclear bone marrow cells, empirical doses ranging from 1 to $4 \times 10^7$ cells have been used. However, different scenarios may require optimization of the amount of cells injected into a tissue of interest. Thus, the quantity of cells to be administered will vary for the subject being treated. In a preferred embodiment, between $10^4$ to $10^8$, more preferably $10^5$ to $10^7$, and most preferably, $3 \times 10^7$ cells and optionally, 50 to 500 µg/kg per day of a cytokine can be administered to a human subject. However, the precise determination of what would be considered an effective dose may be based on factors individual to each patient, including their size, age, size of the infarct or other muscular damage, and amount of time since the damage occurred and factors associated with the mode of delivery (direct injection—lower doses, intravenous—higher doses). Therefore, dosages can be readily ascertained by those skilled in the art from this disclosure and the knowledge in the art.

Another issue regarding the use of stem cells is the purity of the isolated stem cell population. Bone marrow cells, for example, comprise mixed populations of cells, which can be purified to a degree sufficient to produce a desired effect. Those skilled in the art can readily determine the percentage of MAPCs in a population using various well-known methods, such as fluorescence activated cell sorting (FACS). Preferable ranges of purity in populations comprising MAPCs are about 50-55%, 55-60%, and 65-70%. More preferably the purity is about 70-75%, 75-80%, 80-85%; and most preferably the purity is about 85-90%, 90-95%, and 95-100%. However, populations with lower purity can also be useful, such as about 25-30%, 30-35%, 35-40%, 40-45% and 45-50%. Purity of MAPCs can be determined according to the gene expression profile within a population. Dosages can be readily adjusted by those skilled in the art (e.g., a decrease in purity may require an increase in dosage).

The skilled artisan can readily determine the amount of cells and optional additives, vehicles, and/or carrier in compositions and to be administered in methods of the invention. Typically, any additives (in addition to the active stem cell(s) and/or cytokine(s)) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, MAPCs can be administered initially, and thereafter maintained by further administration of MAPCs. For instance, MAPCs can be administered by one method of injection, and thereafter further administered by a different or the same type of method. For example, MAPCs can be administered by surgical myocardial injection to bring cardiovascular function to a suitable level. The patient's levels can then maintained, for example, by intravenous injection, although other forms of administration, dependent upon the patient's condition, can be used.

It is noted that human subjects are treated generally longer than the canines or other experimental animals, such that treatment has a length proportional to the length of the disease process and effectiveness. The doses may be single doses or multiple doses over a period of several days. Thus, one of skill in the art can scale up from animal experiments, e.g., rats, mice, canines and the like, to humans, by techniques from this disclosure and documents cited herein and the knowledge in the art, without undue experimentation. The treatment generally has a length proportional to the length of the disease process and drug effectiveness and the subject being treated.

Examples of compositions comprising MAPCs include liquid preparations for administration, including suspensions; and, preparations for intramuscular or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount, which will achieve the selected viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the MAPCs as described in the present invention.

Those skilled in the art will recognize that the components of the compositions should be selected to be chemically inert. This will present no problem to those skilled in chemical and pharmaceutical principles, or problems can be readily avoided by reference to standard texts or by simple experiments (not involving undue experimentation), from this disclosure and the documents cited herein.

Compositions can be administered in dosages and by techniques well known to those skilled in the medical and veterinary arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, can be ascertained by the skilled artisan, from this disclosure, the documents cited herein, and the knowledge in the art.

MAPCs

Human MAPCs are described in U.S. patent application Ser. Nos. 10/048,757 (PCT/US00/21387 (published as WO 01/11011)) and Ser. No. 10/467,963 (PCT/US02/04652 (published as WO 02/064748)), the contents of which are incorporated herein by reference for their description of MAPCs. MAPCs have been identified in other mammals. Murine MAPCs, for example, are also described in PCT/US00/21387 (published as WO 01/11011) and PCT/US02/04652 (published as WO 02/064748). Rat MAPCs are also described in WO 02/064748.

Isolation and Growth of MAPCs

Methods of MAPC isolation for humans and mouse are known in the art. They are described in PCT/US00/21387 (published as WO 01/11011) and for rat in PCT/US02/04652 (published as WO 02/064748), and these methods, along with the characterization of MAPCs disclosed therein, are incorporated herein by reference.

MAPCs were initially isolated from bone marrow, but were subsequently established from other tissues, including brain and muscle (Jiang Y, et al., Nature. 2002; 418:41-49; Jiang Y, et al., Exp Hematol. 2002b; 30:896-904). Thus, MAPCs can be isolated from multiple sources, including bone marrow, placenta, umbilical cord and cord blood, muscle, brain, liver, spinal cord, blood or skin. For example, MAPCs can be derived from bone marrow aspirates, which can be obtained by standard means available to those of skill in the art (see, for example, Muschler, G. F., et al. *J. Bone Joint Surg. Am.* 1997; 79(11):1699-709; Batinic, D., et al.,

*Bone Marrow Transplant.* 1990; 6(2):103-7) It is, therefore, now possible for one of skill in the art to obtain bone marrow aspirates, brain or liver biopsies, and other organs, and isolate the cells using positive or negative selection techniques available to those of skill in the art, relying upon the genes that are expressed (or not expressed) in these cells (e.g., by functional or morphological assays, such as those disclosed in the above-referenced applications, which have been incorporated herein by reference).

MAPCs from Human Bone Marrow as Described in PCT/US00/21387

Bone marrow mononuclear cells were derived from bone marrow aspirates, which were obtained by standard means available to those of skill in the art (see, for example, Muschler, G. F., et al. *J. Bone Joint Surg. Am.* 1997; 79(11):1699-709; Batinic, D., et al., *Bone Marrow Transplant.* 1990; 6(2):103-7). Multipotent adult stem cells are present within the bone marrow (or other organs such as liver or brain), but do not express the common leukocyte antigen CD45 or erythroblast specific glycophorin-A (Gly-A). The mixed population of cells was subjected to a Ficoll Hypaque separation. The cells were then subjected to negative selection using anti-CD45 and anti-Gly-A antibodies, depleting the population of $CD45^+$ and $Gly-A^+$ cells, and the remaining approximately 0.1% of marrow mononuclear cells were then recovered. Cells could also be plated in fibronectin-coated wells and cultured as described below for 2-4 weeks to deplete the population of cells of $CD45^+$ and $Gly-A^+$ cells.

Alternatively, positive selection could be used to isolate cells via a combination of cell-specific markers. Both positive and negative selection techniques are available to those of skill in the art, and numerous monoclonal and polyclonal antibodies suitable for negative selection purposes are also available in the art (see, for example, Leukocyte Typing V, Schlossman, et al., Eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch, et. al., *J. Immunol. Methods.* 1983; 56:269 (immunoaffinity chromatography), and Wysocki and Sato, *Proc. Natl. Acad. Sci.* (*USA*) 1978; 75:2844 (fluorescence-activated cell sorting).

Recovered $CD45^-/GlyA^-$ cells were plated onto culture dishes coated with 5-115 ng/ml (about 7-10 ng/ml can be used) serum fibronectin or other appropriate matrix coating. Cells were maintained in Dulbecco's Minimal Essential Medium (DMEM) or other appropriate cell culture medium, supplemented with 1-50 ng/ml (about 5-15 ng/ml can be used) platelet-derived growth factor-BB (PDGF-BB), 1-50 ng/ml (about 5-15 ng/ml can be used) epidermal growth factor (EGF), 1-50 ng/ml (about 5-15 ng/ml can be used) insulin-like growth factor (IGF), or 100-10,000 IU (about 1,000 IU can be used) LIF, with $10^{-10}$ to $10^{-8}$ M dexamethasone (or other appropriate steroid), 2-10 µg/ml linoleic acid, and 0.05-0.15 µM ascorbic acid. Other appropriate media include, for example, MCDB, MEM, IMDM, and RPMI. Cells can either be maintained without serum, in the presence of 1-2% fetal calf serum, or, for example, in 1-2% human AB serum or autologous serum.

When re-seeded at $2 \times 10^3$ cells/cm$^2$ every 3 days, >40 cell doublings were routinely obtained, and some populations underwent >70 cell doublings. Cell doubling time was 36-48 h for the initial 20-30 cell doublings. Afterwards cell-doubling time was extended to as much as 60-72 h.

Telomere length of MAPCs from 5 donors (age about 2 years to about 55 years) cultured at re-seeding densities of $2 \times 10^3$ cells/cm$^2$ for 23-26 cell doublings was between 11-13 KB. This was 3-5 KB longer than telomere length of blood lymphocytes obtained from the same donors. Telomere length of cells from 2 donors evaluated after 23 and 25 cell doublings, respectively, and again after 35 cells doublings, was unchanged. The karyotype of these MAPCS was normal.

Phenotype of Human MAPCs Under Conditions Described in PCT/US00/21387

Immunophenotypic analysis by FACS of human MAPCs obtained after 22-25 cell doublings indicated that the cells do not express CD31, CD34, CD36, CD38, CD45, LD50, CD62E and -P, HLA-DR, Muc18, STRO-1, cKit, Tie/Tek; express low levels of CD44, HLA-class I, and β2-microglobulin, express CD10, CD13, CD49b, CD49e, CDw90, Flk1 (N>10).

Once cells underwent >40 doublings in cultures re-seeded at about $2 \times 10^3$/cm$^2$, the phenotype became more homogenous and no cell expressed HLA class-I or CD44 (n=6). When cells were grown at higher confluence, they expressed high levels of Muc18, CD44, HLA class 1 and β2-microglobulin, which is similar to the phenotype described for MSC (N=8) (Pittenger et al. *Science* 1999; 284:143-147).

Immunohistochemistry showed that human MAPCs grown at about $2 \times 10^3$/cm$^2$ seeding density expressed EGF-R, TGF-R1 and -2, BMP-R1A, PDGF-R1a and -B, and that a small subpopulation (between 1 and 10%) of MAPCs stained with anti-SSEA4 antibodies (Kannagi, R. *EMBO J* 1983; 2:2355-61).

Using Clontech cDNA arrays the expressed gene profile of human MAPCs cultured at seeding densities of about $2 \times 10^3$ cells/cm$^2$ for 22 and 26 cell doublings was determined:

A. MAPCs did not express CD31, CD36, CD62E, CD62P, CD44-H, cKit, Tie, receptors for IL1, IL3, IL6, IL11, G CSF, GM-CSF, Epo, Flt3-L, or CNTF, and low levels of HLA-class-I, CD44-E and Muc-18 mRNA.

B. MAPCs expressed mRNA for the cytokines BMP1, BMP5, VEGF, HGF, KGF, MCP1; the cytokine receptors Flk1, EGF-R, PDGF-R1α, gp130, LIF-R, activin-R1 and -R2, TGFR-2, BMP-R1A; the adhesion receptors CD49c, CD49d, CD29; and CD10.

C. MAPCs expressed mRNA for hTRT and TRF1; the POU domain transcription factor Oct-4, sox-2, sox 11 (neural development), sox 9 (chondrogenesis) (Lefebvre V. *Matrix Biol* 1988; 16:529-40); homeodeomain transcription factors: Hoxa4 and -a5 (cervical and thoracic skeleton specification; organogenesis of respiratory tract) (Packer A. I. *Dev Dyn* 2000; 17:62-74), Hox-a9 (myelopoiesis) (Lawrence H. *Blood* 1997; 89:1922), Dlx4 (specification of forebrain and peripheral structures of head) (Akimenko M. A. *J Neurosci* 1994; 14:3475-86), MSX1 (embryonic mesoderm, adult heart and muscle, chondro- and osteogenesis) (Foerst-Potts L. *Dev Dyn* 1997; 209:70-84), PDX1 (pancreas) (Offield M. F. *Development* 1996; 122:983-95).

D. Presence of Oct-4, LIF-R, and hTRT mRNA was confirmed by RT-PCR.

E. In addition, RT-PCR showed that Rex-1 mRNA and Rox-1 mRNA were expressed in MAPCs.

Oct-4, Rex-1 and Rox-1 were expressed in MAPCs derived from human and murine marrow and from murine liver and brain. Human MAPCs expressed LIF-R and stained positive with SSEA-4. Finally, Oct-4, LIF-R, Rex-1 and Rox-1 mRNA levels were found to increase in human MAPCs cultured beyond 30 cell doublings, which resulted in phenotypically more homogenous cells. In contrast, MAPCs cultured at high density lost expression of these markers. This was associated with senescence before 40 cell doublings and loss of differentiation to cells other than chondroblasts, osteoblasts and adipocytes.

Culturing MAPCs as Described in PCT/US00/21387

MAPCs isolated as described herein can be cultured using methods disclosed herein and in PCT/US00/21387, which is incorporated by reference for these methods.

Briefly, for the culture of MAPCs, culture in low-serum or serum-free medium was preferred to maintain the cells in the undifferentiated state. Serum-free medium used to culture the cells, as described herein, was supplemented as described in Table 1. Human MAPCs do not require LIF.

TABLE 1

| | |
|---|---|
| Insulin | 10-50 µg/ml (10 µg/ml)* |
| Transferrin | 0-10 µg/ml (5.5 µg/ml) |
| Selenium | 2-10 ng/ml (5 ng/ml) |
| Bovine serum albumin (BSA) | 0.1-5 µg/ml (0.5 µg/ml) |
| Linoleic acid | 2-10 µl/ml (4.7 µg/ml) |
| Dexamethasone | 0.005-0.15 µM (.01 µM) |
| L-ascorbic acid 2-phosphate | 0.1 mM |
| Low-glucose DMEM (DMEM-LG) | 40-60% (60%) |
| MCDB-201 | 40-60% (40%) |
| Fetal calf serum | 0-2% |
| Platelet-derived growth | 5-15 ng/ml (10 ng/ml) |
| Epidermal growth factor | 5-15 ng/ml (10 ng/ml) |
| Insulin like growth factor | 5-15 ng/ml (10 ng/ml) |
| Leukemia inhibitory factor | 10-10,000 IU (1,000 IU) |

*Preferred concentrations are shown in parentheses.

Addition of 10 ng/mL LIF to human MAPCs did not affect short-term cell growth (same cell doubling time till 25 cell doublings, level of Oct-4 (Oct 3/4) expression). In contrast to what was seen with human cells, when fresh murine marrow mononuclear cells, depleted on day 0 of CD45$^+$ cells, were plated in MAPC culture, no growth was seen. When murine marrow mononuclear cells were plated, and cultured cells 14 days later depleted of CD45$^+$ cells, cells with the morphology and phenotype similar to that of human MAPCs appeared. This suggested that factors secreted by hemopoietic cells were needed to support initial growth of murine MAPCs. When cultured with PDGF-BB and EFG alone, cell doubling was slow (>6 days) and cultures could not be maintained beyond 10 cell doublings. Addition of 10 ng/ml LIF significantly enhanced cell growth.

Once established in culture, cells could be frozen and stored as frozen stocks, using DMEM with 40% FCS and 10% DMSO. Other methods for preparing frozen stocks for cultured cells are also available to those of skill in the art.

Thus, MAPCs could be maintained and expanded in culture medium that is available to the art. Such media include, but are not limited to Dulbecco's Modified Eagle's Medium® (DMEM), DMEM F12 Medium®, Eagle's Minimum Essential Medium®, F-12K Medium®, Iscove's Modified Dulbecco's Medium® and RPMI-1640 Medium®. Many media are also available as a low-glucose formulations, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. It is understood that sera can be heat-inactivated at 55-65° C. if deemed necessary to inactivate components of the complement cascade.

Additional supplements can also be used advantageously to supply the cells with the necessary trace elements for optimal growth and expansion. Such supplements include insulin, transferrin, sodium selenium and combinations thereof. These components can be included in a salt solution such as, but not limited to Hanks' Balanced Salt Solution® (HBSS), Earle's Salt Solution®, antioxidant supplements, MCDB -201® supplements, phosphate buffered saline (PBS), ascorbic acid and ascorbic acid-2-phosphate, as well as additional amino acids. Many cell culture media already contain amino acids, however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin. Antibiotic and antimycotic additives can be of some concern, depending on the type of work being performed. One possible situation that can arise is an antibiotic-containing media wherein bacteria are still present in the culture, but the action of the antibiotic performs a bacteriostatic rather than bacteriocidal mechanism. Also, antibiotics can interfere with the metabolism of some cell types.

Hormones can also be advantageously used in cell culture and include, but are not limited to D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others.

Also contemplated is the use of feeder cell layers. Feeder cells are used to support the growth of fastidious cultured cells, particularly ES cells. Feeder cells are normal cells that have been inactivated by γ-irradiation. In culture, the feeder layer serves as a basal layer for other cells and supplies cellular factors without further growth or division of their own (Lim, J. W. and Bodnar, A., *Proteomics* 2002; 2(9): 1187-1203 (2002)). Examples of feeder layer cells are typically human diploid lung cells, mouse embryonic fibroblasts, Swiss mouse embryonic fibroblasts, but can be any post-mitotic cell that is capable of supplying cellular components and factors that are advantageous in allowing optimal growth, viability, and expansion of stem cells. In many cases, feeder cell layers are not necessary to keep the ES cells in an undifferentiated, proliferative state, as leukemia inhibitory factor (LIF) has anti-differentiation properties. Therefore, supplementation with LIF could be used to maintain MAPC in some species in an undifferentiated state.

Cells in culture can be maintained either in suspension or attached to a solid support, such as extracellular matrix components and synthetic or biopolymers. Stem cells often require additional factors that encourage their attachment to a solid support, such as type I, type II, and type IV collagen, concanavalin A, chondroitin sulfate, fibronectin, "superfibronectin" and fibronectin-like polymers, gelatin, laminin, poly-D and poly-L-lysine, thrombospondin, and vitronectin.

The maintenance conditions of stem cells can also contain cellular factors that allow stem cells, such as MAPCs, to remain in an undifferentiated form. It is advantageous under conditions where the cell must remain in an undifferentiated state of self-renewal for the medium to contain epidermal growth factor (EGF), platelet derived growth factor (PDGF), leukemia inhibitory factor (LIF; in selected species), and combinations thereof. It is apparent to those skilled in the art that supplements that allow the cell to self-renew but not differentiate should be removed from the culture medium prior to differentiation.

Stem cell lines and other cells can benefit from co-culturing with another cell type. Such co-culturing methods arise from the observation that certain cells can supply yet-unidentified cellular factors that allow the stem cell to differentiate into a specific lineage or cell type. These cellular factors can also induce expression of cell-surface receptors, some of which can be readily identified by monoclonal antibodies. Generally, cells for co-culturing are selected based on the type of lineage one skilled in the art wishes to induce, and it is within the capabilities of the skilled artisan to select the appropriate cells for co-culture.

Methods of identifying and subsequently separating differentiated cells from their undifferentiated counterparts can be carried out by methods well known in the art. Cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes (i.e. formation of dendrites and/or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), and enzyme-linked immunosorbent assay (ELISA). From the standpoint of transcriptional upregulation of specific genes, differentiated cells often display levels of gene expression that are different from undifferentiated cells. Reverse-transcription polymerase chain reaction (RT-PCR) can also be used to monitor changes in gene expression in response to differentiation. In addition, whole genome analysis using microarray technology can be used to identify differentiated cells.

Accordingly, once differentiated cells are identified, they can be separated from their undifferentiated counterparts, if necessary. The methods of identification detailed above provide methods of separation, such as FACS, preferential cell culture methods, ELISA, magnetic beads, and combinations thereof. A preferred embodiment of the invention envisions the use of FACS to identify and separate cells based on cell-surface antigen expression.

Additional Culture Methods

In additional experiments it has been found that the density at which MAPCs are cultured can vary from about 100 cells/cm$^2$ or about 150 cells/cm$^2$ to about 10,000 cells/cm$^2$, including about 200 cells/cm$^2$ to about 1500 cells/cm$^2$ to about 2000 cells/cm$^2$. The density can vary between species. Additionally, optimal density can vary depending on culture conditions and source of cells. It is within the skill of the ordinary artisan to determine the optimal density for a given set of culture conditions and cells.

Also, effective atmospheric oxygen concentrations of less than about 10%, including about 3-5%, can be used at any time during the isolation, growth and differentiation of MAPCs in culture.

Inducing MAPCs to Differentiate to Form Committed Progenitors and Tissue-Specific Cell Types Using appropriate growth factors, chemokines, and cytokines, MAPCs can be induced to differentiate to form a number of cell lineages, including, for example, a variety of cells of mesodermal origin as well as cell from neuroectodermal origin (glial cells, oligodendrocytes, and neurons) as well as endodermal origin. These methods are known in the art and are described in both U.S. and PCT applications mentioned above, incorporated by reference for disclosing these methods.

Cardiac muscle differentiation can be accomplished by adding about 5 to about 200 ng/ml (preferably about 100 ng/ml) basic fibroblast growth factor (bFGF) to the standard serum-free culture media without growth factors, as previously described. Confluent MAPCs were exposed to about 2 to 5 µM (preferably about 3 µM) 5-azacytidine and to about $10^{-5}$-$10^{-7}$ M (preferably about $10^{-6}$ M) retinoic acid, and then cultured in MAPC expansion medium afterwards. Alternatively, MAPCs were cultured with either of these inducers alone or a combination of both and then cultured in serum-free medium with about 50-200 ng/mL (preferably about 100 ng/mL FGF2 or a combination of about 5-20 ng/mL (preferably about 10 ng/mL) BMP-4 and about 100 ng/mL FGF2. Expression of proteins consistent with cardiomyocytes was found. Gata4 and Gata6 were expressed as early as day 2 and persisted till day 15. Cardiac troponin-T was expressed after day 4 and cardiac troponin-I from day 6 on, while we could detect ANP after day 11. These cardiac proteins were detected in >70% of cells by immunohistochemistry on day 15. The transcription factor Myf6 was found from day 2 on. Expression of desmin started on day 6 and myogenin on day 2. Skeletal actin was also found. When the cultures were maintained for >3 weeks, cells formed syncitia. There also were infrequent spontaneous contractions occurring in the cultures, which were propagated over several mm distance.

Endothelial Cells MAPCs express Flk1 but not CD34, PECAM, E- and P-selectin, CD36, Tie/Tek or Flt1. When MAPCs were cultured in serum-free MAPC medium with about 20 ng/mL VEGF, CD34 appeared on the cell surface and cells expressed vWF by day 14 (immunofluorescence). In addition, cells expressed Tie, Tek, Flk1 and Flt1, PECAM, P-selectin and E-selectin, and CD36. Results from the histochemical staining were confirmed by Western blot. When VEGF induced cells were cultured on matrigel or collagen type IV, vascular tube formation was seen.

Approaches for transplantation to prevent immune rejection:

In some embodiments, it may be desired that the MAPCs (or differentiated progeny thereof) be treated or otherwise altered prior to transplantation/administration in order to reduce the risk of stimulating host immunological response against the transplanted cells. Any method known in the art to reduce the risk of stimulating host immunological response may be employed. The following provides a few such examples.

a. Universal donor cells: MAPC have cell surface profiles consistent with evasion of immune recognition, and in their natural state may not stimulate immune sensitization and rejection. They may serve as natural universal donor cells even if their progeny mature to cells which ordinarily would be immune-recognized and rejected.

Alternatively, MAPC also can be manipulated to serve as universal donor cells. MAPCs can be modified to serve as universal donor cells by eliminating HLA-type I and HLA-type II antigens, and potentially introducing the HLA-antigens from the prospective recipient to avoid that the cells become easy targets for NK-mediated killing, or become susceptible to unlimited viral replication and/or malignant transformation. Elimination of HLA-antigens can be accomplished by homologous recombination or via introduction of point-mutations in the promoter region or by introduction of a point mutation in the initial exon of the antigen to introduce a stop-codon, such as with chimeroplasts. Transfer of the host HLA-antigen can be achieved by retroviral, lentiviral, adeno associated virus or other viral transduction or by transfection of the target cells with the HLA-antigen cDNAs. MAPC can be used to establish and set amount or a given range or level of a protein in the body or blood.

b. Gene therapy: MAPCs can be extracted and isolated from the body, grown in culture in the undifferentiated state or induced to differentiate in culture, and genetically altered using a variety of techniques, especially viral transduction. Uptake and expression of genetic material is demonstrable, and expression of foreign DNA is stable throughout development. Retroviral and other vectors for inserting foreign DNA into stem cells are known to those of skill in the art. (Mochizuki, H. et al (1998) *J. Virol* 72(11): 8873-8883; Robbins, P. et al (1997) *J. Virol.* 71(12): 9466-9474; Bierhuizen, M. et al (1997) *Blood* 90(9): 3304-3315; Douglas, J. et al (1999) *Hum. Gene Ther.* 10(6): 935-945; Zhang, G. et al (1996) *Biochem. Biophys. Res. Commun.* 227(3): 707-711). Once transduced using a retroviral vector, enhanced green fluorescent protein (eGFP) expression persists in terminally differentiated muscle cells, endothelium, and c-Kit positive cells derived from the isolated MAPCs, demonstrating that expression of retroviral vectors introduced into MAPC persists throughout differentiation. Terminal differentiation was induced from cultures initiated with 10 eGFP$^+$ cells previously transduced by retroviral vector and sorted a few weeks into the initial MAPC culture period.

c. Development of Hematopoietic Cells: MAPCs can be administered (e.g., intravenously) to establish hematopoiesis (the process by which blood cells are formed). Once the administered MAPCs have generated blood cells and the subject has accepted the blood type of MAPC derived blood cells, the subject may no longer reject additional MAPCs or progeny or tissue derived therefrom.

d. Encapsulation: In some embodiments, the MAPCs are encapsulated. The primary goal in encapsulation as a cell therapy is to protect allogeneic and xenogeneic cell transplants from destruction by the host immune response, thereby eliminating or reducing the need for immuno-suppressive drug therapy. Techniques for microencapsulation of cells are known to those of skill in the art (see, for example, Chang, P., et al., *Trends in Biotech.*, 17:78-83 (1999); Matthew, H. W., et al., ASAIO Trans, 37(3):M328-30 (1991); Yanagi, K., et al., *ASAIO Trans.*, 35(3):570-2 (1989); Cai Z. H., et al., *Artif Organs*, 12(5):388-93 (1988); Chang, T. M., *Artif Organs*, 16(1):71-4 (1992)). Materials for microencapsulation of cells include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. U.S. Pat. No. 5,639,275, for example, describes improved devices and methods for long-term, stable expression of a biologically active molecule using a biocompatible capsule containing genetically engineered cells.

Additionally, the MAPCs may be encapsulated by membranes prior to implantation. The encapsulation provides a barrier to the host's immune system and inhibits graft rejection and inflammation. It is contemplated that any of the many methods of cell encapsulation available may be employed. In some instances, cells are individually encapsulated. In other instances, many cells are encapsulated within the same membrane. In embodiments in which the cells are removed following implantation, the relatively large size of a structure encapsulating many cells within a single membrane provides a convenient means for retrieval of the implanted cells. Several methods of cell encapsulation are available to the art, such as those described in European Patent Publication No. 301,777 or U.S. Pat. Nos. 4,353,888; 4,744,933; 4,749,620; 4,814,274; 5,084,350; 5,089,272; 5,578,442; 5,639,275; and 5,676,943, each of which is incorporated herein by reference.

e. Natural Killer (NK) Cell Function: Any means which inhibits NK cell function or depletes NK cells from a population of cells may also be administered to prevent immune rejection, increase engraftment and/or increase immune tolerance. Such an agent includes an anti-NK cell antibody or irradiation or any other material which can inhibit NK cell function or deplete NK cells from a population.

Monitoring of Subject after Administration of MAPCs

Following transplantation, the growth and/or differentiation of the administered MAPCs or differentiated progeny, and the therapeutic effect of the MAPCs or progeny may be monitored. Additionally, following administration, the immunological tolerance of the subject to the MAPCs or progeny derived therefrom may be tested by various methods known in the art to assess the subject's immunological tolerance to MAPCs. In cases where subject tolerance of MAPCs is suboptimal (e.g., the subject's immune system is rejecting the exogenous MAPCs), therapeutic adjunct immunosuppressive treatment, which is known in the art, of the subject may be performed.

Genetically-Modified Stem Cells

MAPCs can be genetically altered ex vivo, eliminating one of the most significant barriers for gene therapy. For example, a subject's bone marrow aspirate is obtained, and from the aspirate MAPCs are isolated. The MAPCs are then genetically altered to express one or more desired gene products. The MAPCs can then be screened or selected ex vivo to identify those cells which have been successfully altered, and these cells can be reintroduced into the subject, either locally or systemically. Alternately, MAPCs can be genetically altered and cultured to induce differentiation to form a specific cell lineage for transplant. In either case, the transplanted MAPCs provide a stably-transfected source of cells that can express a desired gene product. Especially where the patient's own bone marrow aspirate is the source of the MAPCs, this method provides an immunologically safe method for producing transplant cells.

Methods for Genetically Altering MAPCs

Cells isolated by the methods described herein can be genetically modified by introducing DNA or RNA into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, nucleofection or direct "naked" DNA transfer. MAPCs can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) expression in specific cell compartments (including but not limited to the cell membrane).

Homologous recombination

Calcium phosphate transfection, which relies on precipitates of plasmid DNA/calcium ions, can be used to introduce plasmid DNA containing a target gene or polynucleotide into isolated or cultured MAPCs. Briefly, plasmid DNA is mixed into a solution of calcium chloride, then added to a solution which has been phosphate-buffered. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e.g., ProFection® from Promega Corp., Madison, Wis.).

DEAE-dextran transfection, which is also known to those of skill in the art, may be preferred over calcium phosphate transfection where transient transfection is desired, as it is often more efficient.

Since the MAPC are isolated cells, microinjection can be particularly effective for transferring genetic material into the cells. Briefly, cells are placed onto the stage of a light microscope. With the aid of the magnification provided by the microscope, a glass micropipette is guided into the nucleus to inject DNA or RNA. This method is advantageous because it provides delivery of the desired genetic material directly to the nucleus, avoiding both cytoplasmic and lysosomal degradation of the injected polynucleotide. This technique has been used effectively to accomplish germline modification in transgenic animals.

MAPC can also be genetically modified using electroporation. The target DNA or RNA is added to a suspension of cultured cells. The DNA/RNA-cell suspension is placed between two electrodes and subjected to an electrical pulse, causing a transient permeability in the cell's outer membrane that is manifested by the appearance of pores across the membrane. The target polynucleotide enters the cell through the open pores in the membrane, and when the electric field is discontinued, the pores close in approximately one to 30 minutes.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPC) can be added. A recommended reagent for liposomal transfer is Lipofectin® (Life Technologies, Inc.), which is commercially available. Lipofectin®, for example, is a mixture of the cationic lipid N-[1-(2,3-dioleyloyx) propyl]-N—N—N-trimethyl ammonia chloride and DOPE. Delivery of linear DNA, plasmid DNA, or RNA can be accomplished either in vitro or in vivo using liposomal delivery, which may be a preferred method due to the fact that liposomes can carry larger pieces of DNA, can generally protect the polynucleotide from degradation, and can be targeted to specific cells or tissues. A number of other delivery systems relying on liposomal technologies are also commercially available, including Effectene™ (Qiagen), DOTAP (Roche Molecular Biochemicals), FuGene 6™ (Roche Molecular Biochemicals), and Transfectam® (Promega). Cationic lipid-mediated gene transfer efficiency can be enhanced by incorporating purified viral or cellular envelope components, such as the purified G glycoprotein of the vesicular stomatitis virus envelope (VSV-G), in the method of Abe, A., et al. (*J. Virol.* (1998) 72: 6159-6163).

Gene transfer techniques which have been shown effective for delivery of DNA into primary and established mammalian cell lines using lipopolyamine-coated DNA can be used to introduce target DNA into MAPCs. This technique is generally described by Loeffler, J. and Behr, J (*Methods in Enzymology* (1993) 217: 599-618).

Naked plasmid DNA can be injected directly into a tissue mass formed of differentiated cells from the isolated MAPCs. This technique has been shown to be effective in transferring plasmid DNA to skeletal muscle tissue, where expression in mouse skeletal muscle has been observed for more than 19 months following a single intramuscular injection. More rapidly dividing cells take up naked plasmid DNA more efficiently. Therefore, it is advantageous to stimulate cell division prior to treatment with plasmid DNA.

Microprojectile gene transfer can also be used to transfer genes into MAPCs either in vitro or in vivo. The basic procedure for microprojectile gene transfer was described by J. Wolff (*Gene Therapeutics* (1994) at page 195). Briefly, plasmid DNA encoding a target gene is coated onto microbeads, usually 1-3 micron sized gold or tungsten particles. The coated particles are placed onto a carrier sheet inserted above a discharge chamber. Once discharged, the carrier sheet is accelerated toward a retaining screen. The retaining screen forms a barrier which stops further movement of the carrier sheet while allowing the polynucleotide-coated particles to be propelled, usually by a helium stream, toward a target surface, such as a tissue mass formed of differentiated MAPCs. Microparticle injection techniques have been described previously, and methods are known to those of skill in the art (see Johnston, S. A. et al (1993) *Genet. Eng.* (NY) 15: 225-236; Williams, R. S. et al (1991) *Proc. Natl. Acad. Sci. USA* 88: 2726-2730; Yang, N. S. et al (1990) *Proc. Natl. Acad. Sci. USA* 87: 9568-9572).

Signal peptides can be attached to plasmid DNA, as described by Sebestyen et al. (*Nature Biotech.* (1998) 16: 80-85), to direct the DNA to the nucleus for more efficient expression.

Viral vectors are used to genetically alter MAPCs and their progeny. Viral vectors are used, as are the physical methods previously described, to deliver one or more target genes, polynucleotides, antisense molecules, or ribozyme sequences, for example, into the cells. Viral vectors and methods for using them to deliver DNA to cells are well known to those of skill in the art. Examples of viral vectors which can be used to genetically alter the cells of the present invention include, but are not limited to, adenoviral vectors, adeno-associated viral vectors, retroviral vectors (including lentiviral vectors), alphaviral vectors (e.g., Sindbis vectors), and herpes virus vectors.

Retroviral vectors are effective for transducing rapidly-dividing cells, although a number of retroviral vectors have been developed to effectively transfer DNA into non-dividing cells as well (Mochizuki, H. et al (1998) *J. Virol.* 72: 8873-8883). Packaging cell lines for retroviral vectors are known to those of skill in the art. Packaging cell lines provide the viral proteins needed for capsid production and virion maturation of the viral vector. Generally, these include the gag, pol, and env retroviral genes. An appropriate packaging cell line is chosen from among the known cell lines to produce a retroviral vector which is ecotropic, xenotropic, or amphotropic, providing a degree of specificity for retroviral vector systems.

A retroviral DNA vector is generally used with the packaging cell line to produce the desired target sequence/vector combination within the cells. Briefly, a retroviral DNA vector is a plasmid DNA which contains two retroviral LTRs positioned about a multicloning site and SV40 promoter so that a first LTR is located 5 to the SV40 promoter, which is operationally linked to the target gene sequence cloned into the multicloning site, followed by a 3' second LTR. Once formed, the retroviral DNA vector can be transferred into the packaging cell line using calcium phosphate-mediated transfection, as previously described. Following approximately 48 hours of virus production, the viral vector, now containing the target gene sequence, is harvested.

Targeting of retroviral vectors to specific cell types was demonstrated by Martin, F., et al., (*J. Virol.* (1999) 73: 6923-6929), who used single-chain variable fragment antibody directed against the surface glycoprotein high-molecular-weight melanoma-associated antigen fused to the amphotropic murine leukemia virus envelope to target the vector to delivery the target gene to melanoma cells. Where targeted delivery is desired, as, for example, when differentiated cells are the desired objects for genetic alteration, retroviral vectors fused to antibody fragments directed to the specific markers expressed by each cell lineage differentiated from the MAPCs can be used to target delivery to those cells.

Lentiviral vectors are also used to genetically alter MAPCs. Many such vectors have been described in the literature and are known to those of skill in the art (Salmons, B. and Gunzburg, W. H. (1993) *Hum. Gene Therapy* 4: 129-141. These vectors have been effective for genetically altering human hematopoietic stem cells (Sutton, R., et al (1998) *J. Virol.* 72: 5781-5788). Packaging cell lines have been described for lentivirus vectors (see Kafri, T., et al (1999) *J. Virol.* 73: 576-584; Dull, T., et al (1998) *J. Virol.* 72: 8463-8471).

Recombinant herpes viruses, such as herpes simplex virus type I (HSV-1) have been used successfully to target DNA delivery to cells expressing the erythropoietin receptor (Laquerre, S., et al (1998) *J. Virol.* 72: 9683-9697). These vectors can also be used to genetically alter the MAPCs, which the inventors have demonstrated to be stably transduced by a viral vector.

Adenoviral vectors have high transduction efficiency, can incorporate DNA inserts up to 8 Kb, and can infect both replicating and differentiated cells. A number of adenoviral vectors have been described in the literature and are known to those of skill in the art (see, for example, Davidson, B. L., et al (1993) *Nature Genetics* 3: 219-223; Wagner, E., et al (1992) *Proc. Natl. Acad. Sci. USA* 89: 6099-6103). Methods for inserting target DNA into an adenovirus vector are known to those of skill in the art of gene therapy, as are methods for using recombinant adenoviral vectors to introduce target DNA into specific cell types (Wold, W (1998) *Humana Methods in Molecular Medicine*, Blackwell Science, Ltd.). Binding affinity for certain cell types has been demonstrated by modification of the viral vector fiber sequence. Adenovirus vector systems have been described which permit regulated protein expression in gene transfer (Molin, M., et al (1998) *J. Virol.* 72: 8358-8361). A system has also been described for propagating adenoviral vectors with genetically modified receptor specificities to provide transductional targeting to specific cell types (Douglas, J., et al (1999) *Nature Biotech.* 17: 470-475). Recently described ovine adenovirus vectors even address the potential for interference with successful gene transfer by preexisting humoral immunity (Hofmann, C., et al (1999) *J. Virol.* 73: 6930-6936).

Adenovirus vectors are also available which provide targeted gene transfer and stable gene expression using molecular conjugate vectors, constructed by condensing plasmid DNA containing the target gene with polylysine, with the polylysine linked to a replication-incompetent adenovirus. (Schwarzenberger, P., et al (1997) *J. Virol.* 71: 8563-8571.)

Alphavirus vectors, particularly the Sindbis virus vectors, are also available for transducing the cells of the present invention. These vectors are commercially available (Invitrogen, Carlsbad, Calif.) and have been described in, for example, U.S. Pat. No. 5,843,723, as well as by Xiong, C., et al (1989) *Science* 243: 1188-1191; Bredenbeek, P. J., et al (1993) 6 J. Virol. 7: 6439-6446; and Frolov, I., et al (1996) *Proc. Natl. Acad. Sci. USA* 93: 11371-11377.

The inventors have shown that MAPC possess good transduction potential using the eGFP-MND lentiviral vector described by Robbins, et al. (*J. Virol.* (1997) 71(12): 9466-9474) and eGFP-MGF vector. Using this method, 30-50% of MAPC can be transduced after a short exposure of 4.6 hours to an enhanced green fluorescent protein (eGFP) vector containing supernatants made in PA3-17 packaging cells (an amphotropic packaging cell line derived from NIH 3T3 fibroblasts and described by Miller, A. D., and C. Buttimore (*Mol. Cell. Biol.* (1986) 6: 2895-2902), combined with protamine (8 mg/ml). Expression of eGFP persists throughout the culture of undifferentiated MAPC. In addition, transfection using lipofectamine has been successfully used to introduce transgenes in MAPCs.

Successful transfection or transduction of target cells can be demonstrated using genetic markers, in a technique that is known to those of skill in the art. The green fluorescent protein of *Aequorea victoria*, for example, has been shown to be an effective marker for identifying and tracking genetically modified hematopoietic cells (Persons, D., et al (1998) *Nature Medicine* 4:1201-1205). Alternative selectable markers include the β-Gal gene, the truncated nerve growth factor receptor, drug selectable markers (including but not limited to NEO, MTX, hygromycin).

Any of these techniques can also be applied to introducing a transcriptional regulatory sequence into MAPC to activate a desired endogenous gene. This can be done by both homologous (e.g., U.S. Pat. No. 5,641,670) or non-homologous (e.g., U.S. Pat. No. 6,602,686) recombination. These are incorporated by reference for teaching of methods of endogenous gene activation.

Use of Stem Cells

In the case of cardiac disease, diseases which can be treated using MAPC or progeny therefrom include, but are not limited to, myocarditis, cardiomyopathy, heart failure, damage caused by heart attacks, hypertension, atherosclerosis or heart valve dysfunction. Progeny can include cardiomyocytes that repopulate the injured tissue or endothelial cells that provide neo-vascularization to the tissue.

MAPC can also be administered to provide vasculature in subjects suffering from a loss and/or function of vascularization as a result of physical or disease related damage. Disease states characterized by a loss of vascularization and/or function, and that benefit from methods of the present invention include vascular conditions, such as ischemia (including ischemia-reperfusion injury), congestive heart failure, peripheral vasculature disorder, coronary vascular disease, diabetic ulcers, pressure ulcers, hypertension, stroke, aneurysm, thrombosis, arrhythmia, tachycardia, or surgical or physical (e.g., wounding) trauma.

MAPCs can be used to repopulate heart muscle cells by either direct injection into the area of tissue damage or by systemic injection, allowing the cells to home to the cardiac tissues. This method can be particularly effective if combined with angiogenesis. Both the methods of injection and methods for promoting angiogenesis are known to those of skill in the art. MAPCs provide a broader differentiation range to provide a more varied source of cells for cardiac or other tissue repair utilizing these techniques.

For the purposes described herein, either autologous or allogeneic MAPCs can be administered to a patient, either in differentiated or undifferentiated form, genetically altered or unaltered, by direct injection to a tissue site, systemically, on or around the surface of an acceptable matrix, or in combination with a pharmaceutically acceptable carrier.

In the case of degenerative myocardial disease, MAPCs provide for both myocyte replacement and stimulation of angioneogenesis. Improved cardiac function can be indicated, for example, by increased perfusion. This therapy can be used as a stand-alone therapy or in conjunction with revascularization therapies. MAPCs offer the advantage of forming vascular structures to furnish and supply blood to the emerging cardiac muscle mass.

In one embodiment, the present invention comprises methods of increasing cardiac function in a subject by administering a suitable amount of MAPCs to the subject, wherein MAPCs incorporate into existing cardiac tissues and generate new cardiac muscle.

Cardiac diseases treatable with MAPC-based therapies include, but are not limited to, congestive heart failure, coronary artery disease, myocardial infarction, myocardial ischemia, atherosclerosis, cardiomyopathy, cardiac arrhythmias, muscle mass abnormalities, and congenital heart disease.

Myocardial infarction (MI) is characterized by the death of myocytes, by coagulative necrosis, myocytolysis, contraction band necrosis, or apoptosis, resulting from a critical imbalance between the oxygen supply and demand of the myocardium. The most common cause of MI is coronary artery thrombosis following the rupture of atheromatous plaques in epicardial blood vessels resulting in regional myocardial ischemia. Scar formation in the infarcted region impairs cardiac function.

Cardiac injury, such as MI, promotes tissue responses that enhance myogenesis using implanted MAPCs. Thus, administration of MAPCs can, for example, reduce the degree of scar formation, augment ventricular function and compensate for weakened cardiac muscle, thereby improving cardiac function. New muscle is thereby created within an infarcted myocardial segment. Preferably, MAPCs can be directly infiltrated into the zone of infarcted tissue.

MAPCs, as well as damaged cardiac tissues, secrete cytokines that have beneficial effects, including recruitment of reparative cells (e.g., MAPCs, hematopoietic, mesenchymal stem cells) to the damaged tissue by "homing" mechanisms and modulation of inflammatory processes. Homing of cells that can advantageously repair myocardium, such as MAPCs, can be preferentially induced by co-administration of cytokines. MAPCs can also promote angiogenesis, which further enhances tissue repair.

In the past, the prevention of progression to end stage congestive heart failure was believed to preventable only by minimizing loss of myocyte mass. Indeed, left ventricular dysfunction is the strongest predictor of negative outcome following MI. Current treatment focuses on limiting myocyte death, but offers little to replace those myocytes that have already been destroyed. Additionally, other forms of heart failure resulting from cell death/loss not associated with ischemia can not be corrected by additional perfusion, but instead require restoration of functional muscle mass. These diseases include, but are not limited to, correction of congenital abnormalities, infective myocarditis induced by viral means (HIV, Coxsackieviruses A and B), protozoa (Chagas Disease), bacteria, and idiopathic cardiomyopathies. In addition, drugs or toxins, such as those used in chemotherapy can also induce myocyte death. These include, but are not limited to, doxirubicin, adriamycin, and catecholamines. Bacterial toxins can also cause death of muscle tissues. Hypersensitivity myocarditis and autoimmune endocarditis is another disease that can be treated advantageously using the methods of the present invention. SLE and Sarcoidosis may also be treated using progenitor cell-based therapies.

MAPC-based therapies are not limited to improvement of cardiac pathology, but can be extended to any type of degenerative muscular disorder in which the primary pathology is loss of striated muscle mass and/or function. This would include, but is not limited to, muscular dystrophies, trauma, and myasthenia gravis. Thus, in another embodiment, the present invention comprises methods of increasing striated muscle tissue mass by contacting a suitable amount of MAPCs with existing striated muscle tissue and generating viable striated muscle tissue.

Detection of Myocardial Engraftment

Engraftment and repopulation of striated muscle tissue by evaluating muscle function can be monitored using various well-known imaging techniques such as scintigraphy, myocardial perfusion imaging, gated cardiac blood-pool imaging, first-pass ventriculography, right-to-left shunt detection, positron emission tomography, single photon emission computed tomography, magnetic resonance imaging, harmonic phase magnetic resonance imaging, echocardiography, and myocardial perfusion reserve imaging.

Cardiac scintigraphy evaluates myocardial perfusion and/or function to detect physiologic and anatomic abnormalities of the heart. There are five major classes of cardiac scintigraphy: myocardial perfusion imaging, gated cardiac blood-pool imaging, first-pass cardiac imaging, myocardial infarction imaging, and right-to-left shunt evaluation (American College of Radiology Standard for the Performance of Cardiac Scintigraphy).

Myocardial perfusion imaging is primarily used to detect the presence, location, and extent of coronary artery disease by evaluating the physiologic significance or sequelae of known or suspected coronary artery stenosis, monitoring the effects of treatment of coronary artery disease, including revascularization and medical therapy. Myocardial perfusion imaging is also useful for detecting acute myocardial infarction and prognosis after infarction, for evaluating the viability of dysfunctional myocardium, for determining the risk of myocardial events, and for evaluating ventricular function.

An echocardiogram is a test in which ultrasound is used to examine the heart. In addition to providing single-dimension images, known as M-mode echo that allows accurate measurement of the heart chambers, the echocardiogram also offers two-dimensional (2-D) Echo and is capable of displaying a cross-sectional "slice" of the beating heart, including the chambers, valves and the major blood vessels that exit from the left and right ventricle.

Doppler is a special part of the ultrasound examination that assesses blood flow (direction and velocity). In contrast, the M-mode and 2-D Echo evaluates the size, thickness and movement of heart structures (chambers, valves, etc.). During the Doppler examination, the ultrasound beams will evaluate the flow of blood as it makes it way though and out of the heart. This information is presented visually on the monitor (as color images or grayscale tracings and also as a series of audible signals with a swishing or pulsating sound).

Echocardiography provides important information about, among other structures and functions, the size of the chambers of the heart, including the dimension or volume of the cavity and the thickness of the walls. The appearance of the walls may also help identify certain types of heart disease that predominantly involve the heart muscle. Pumping function of the heart can also be assessed by echocardiography. One can tell if the pumping power of the heart is normal or reduced to a mild or severe degree. This measure is known as an ejection fraction or EF. A normal EF is around 55 to 65%. Numbers below 45% usually represent some decrease in the pumping strength of the heart, while numbers below 30 to 35% are representative of an important decrease. Echocardiography can also identify if the heart is pumping poorly due to a condition known as cardiomyopathy, or if one or more isolated areas have depressed movement due to prior heart attacks. Thus, echocardiography can assess the pumping ability of each chamber of the heart and also the movement of each visualized wall. The decreased movement, in turn, can be graded from mild to severe. In extreme cases, an area affected by a heart attack may have no movement (akinesia), or may even bulge in the opposite direction (dyskinesia). The latter is seen in patients with aneurysm of the left ventricle or LV.

Echocardiography identifies the structure, thickness and movement of each heart valve. It can help determine if the valve is normal, scarred from an infection or rheumatic fever, thickened, calcified, torn, etc. It can also assess the function of prosthetic or artificial heart valves. The additional use of Doppler helps to identify abnormal leakage across heart valves and determine their severity. Doppler is also very useful in diagnosing the presence and severity of valve stenosis or narrowing. Unlike echocardiography, Doppler follows the direction and velocity of blood flow rather than the movement of the valve leaflets or components. Thus, reversed blood direction is seen with leakages while increased forward velocity of flow with a characteristic pattern is noted with valve stenosis.

Echocardiography is used to diagnose mitral valve prolapse (MVP), while Doppler identifies whether it is associated with leakage or regurgitation of the mitral valve (MR). The presence of MR frequently prompts the use of antibiotics prior to any dental or non-sterile surgical procedure. Such action helps reduce the rare complication of valve infection.

The volume status of blood vessels can also be monitored by echocardiography. Low blood pressure can occur in the setting of poor heart function but may also be seen when patients have a reduced volume of circulating blood (as seen with dehydration, blood loss, use of diuretics or "water pill", etc.). In many cases, the diagnosis can be made on the basis of history, physical examination and blood tests. However, confusion may be caused when patients have a combination of problems. Echocardiography may help clarify the confusion. The inferior vena cava (the major vein that returns blood from the lower half of the body to the right atrium) is distended or increased in size in patients with heart failure and reduced in caliber when the blood volume is reduced. Echocardiography is useful in the diagnosis of fluid in the pericardium. It also determines when the problem is severe and potentially life threatening. Other diagnoses made by Doppler or echocardiography include congenital heart diseases, blood clots or tumors within the heart, active infection of the heart valves, abnormal elevation of pressure within the lungs, among others.

Myocardial perfusion reserve (MPR) quantifies the capacity of the circulatory response to a maximal increase in physiological demand (Siebert, J. E., et al (2002) *Proc. Intl. Soc. Mag. Reson. Med.* vol. 10). MPR indicates the net circulatory consequence from coronary lesions and other vascular states, regardless of their morphological appearance, including the compensation by collateral circulation. Current perfusion acquisition methods now provide adequate temporal and spatial resolution, SNR, and first-pass contrast enhancement ratio.

MPR image calculation challenges: 1) cardiac phase shifts between stress and rest acquisitions, 2) stress-rest difference in diaphragm position, 3) cardiac phase jitter that introduces variability in LV edge features. Stress-rest mismatches of myocardial anatomy and the reliability of the input function normalization may pose the ultimate limitation of MPR imaging. Intensity correction of surface coil reception modulations is required to determine the input function normalization, for post-processing automation, to improve the qualitative assessment of cardiac perfusion images, movie loops, and time-intensity curves during interactive review of MPR quantitative images. Given the integrative and objective MPR images, interactive investigation of suspicious regions in the thresholded MPR image forms the core of perfusion exam interpretation. MPR imaging may provide quantitative, objective information to reduce variability in perfusion exam interpretation, and to document MR myocardial perfusion.

The present invention is additionally described by way of the following illustrative, non-limiting Examples.

EXAMPLES

Example 1

Isolation of Human MAPCs from Bone Marrow Mononuclear Cells

Bone marrow mononuclear cells were obtained from bone marrow aspirates from the posterior iliac crest of >80 healthy human volunteers. Ten to 100 cubic centimeters of bone marrow was obtained from each subject, as shown in Table 2, which indicates the approximate number of mononuclear cells isolated from each subject. Mononuclear cells (MNC) were obtained from bone marrow by centrifugation over a Ficoll-Paque density gradient (Sigma Chemical Co, St Louis, Mo.). Bone marrow MNC were incubated with CD45 and Glycophorin A microbeads (Miltenyi Biotec, Sunnyvale, Calif.) for 15 minutes and $CD45^+/Gly-A^+$ cells removed by placing the sample in front of a SuperMACS magnet. The eluted cells are 99.5% $CD45^-/GlyA^-$.

As shown in Table 2, depletion of $CD45^+$ $GlyA^+$ cells resulted in recovery of $CD45^-$ $GlyA^-$ cells which constituted approximately 0.05 to 0.10% of the total bone marrow mononuclear cells.

TABLE 2

| Volume of Bone Marrow (cc) | Number of mononuclear BM cells post ficoll | Number of 45$^-$/GlyA$^-$ cell post-MACS | Number of MAPCs (estimated by limiting dilution assay, LDA) |
| --- | --- | --- | --- |
| 50 | 100 millions | 100,000 | 50 |
| 25 | 80 | 60,000 | 35 |
| 25 | 50 | 14,000 | 10 |
| 50 | 100 | 50,000 | 30 |
| 10 | 150 | 75,000 | 30 |
| 30 | 100 | 100,000 | 25 |
| 25 | 80 | 75,000 | 35 |
| 100 | 190 | 78,000 | 25 |
| 100 | 150 | 60,000 | 15 |
| 100 | 160 | 160,000 | 85 |
| 100 | 317 | 400,000 | 50 |
| 100 | 200 | 150,000 | 70 |
| 50 | 160 | 160,000 | 85 |
| 50 | 115 | 150,000 | 70 |
| 25 | 60 | 60,000 | 30 |
| 100 | 307 | 315,000 | 100 |
| 100 | 216 | 140,000 | 80 |
| 50 | 130 | 150,000 | 40 |
| 100 | 362 | 190,000 | 60 |
| 50 | 190 | 150,000 | 40 |
| 100 | 200 | 185,000 | 100 |
| 100 | 387 | 300,000 | 170 |
| 50 | 100 | 130,000 | 20 |
| 150 | 588 | 735,000 | 300 |

Cells were selected that do not express the common leukocyte antigen, CD45, or the erythroid precursor marker, glycophorin-A (GlyA). $CD45^-GlyA^-$ cells constitute $1/10^3$ marrow mononuclear cells. $CD45^-GlyA^-$ cells were plated in wells coated with fibronectin in with 2% FCS, and EGF, PDGF-BB, dexamethasone, insulin, linoleic acid, and ascorbic acid. After 7-21 days, small clusters of adherent cells developed. Using limiting dilution assays, the frequency of cells giving rise to these adherent clusters is $1/5 \times 10^3$ $CD45^-GlyA^-$ cells.

When colonies appeared (about $10^3$ cells) cells were recovered by trypsinization and re-plated every 3-5 days at a 1:4 dilution under the same culture conditions. Cell densities were maintained between about $2-8 \times 10^3$ cells/cm$^2$. Cell doubling time was 48-60 h. Immunophenotypic analysis by FACS of cells obtained after 10-12 cell doubling showed that cells did not express CD31, CD34, CD36, CD38, CD45, CD50, CD62E and CD62-P, Muc18, cKit, Tie/Tek, and CD44. Cells expressed no HLA-DR or HLA-class-I and expressed low levels of β2-microglobulin. Cells stained highly positive with antibodies against CD10, CD13, CD49b, CD49e, CDw90, Flk1. The MAPC phenotype remained unchanged for >30 cell doublings (n=15). MAPC cultures with cells capable of proliferating beyond 30 cell doublings and differentiating to all mesodermal cell-types have been established from >85% of donors, age 2-50 years. In 10 donors, MAPC were expanded for >50 cell doublings. When cells were cultured in serum-free medium, also supplemented with 10 ng/mL IGF, cell doubling was slower (>60 h), but >40 cell doublings could be obtained. As was seen for cells cultured with 2% FCS without IGF, cells cultured in serum-free medium were HLA-class-I and CD44 negative, and could differentiate into all mesodermal phenotypes.

Telomere length of MAPC from 5 donors (age 2-50 years) cultured for 15 cell doublings was between about 11-16 kB. In 3 donors, this was about 3 kB longer than telomere length of blood lymphocytes obtained from the same donors. Telomere length of cells from 1 donor evaluated after 15 cell doublings, 30 cells doublings and 45 cell doublings remained unchanged. Cytogenetic analysis of MAPC recovered after 30 cell doublings showed a normal karyotype.

Example 2

Treatment of Acute MI in Rat LAD Model

Cell Isolation and Expansion of Rat MAPC

BM and MNC from Sprague Dawley or Wistar rats were obtained and plated under conditions similar for mMAPC. After 21-28 days, cells were depleted of $CD45^+$ cells, and the resulting $CD45^-$ cells were subcultured at 10 cells/well.

Similar to mMAPC, rMAPC have been culture expanded for >100 PDs. Expansion conditions of rat MAPC culture required the addition of EGF, PDGF-BB and LIF and culture on FN, but not collagen type I, laminin or Matrigel™

Rat MAPC that had undergone 42 PDs, 72 PDs, 80 PDs, and 100 PDs, were harvested and telomere lengths evaluated. Telomeres did not shorten in culture, as was determined by Southern blot analysis after 42 PDs, 72 PDs, 80 PDs, and 100 PDs. Monthly cytogenetic analysis of rat MAPC revealed normal karyotype.

Transduction

To demonstrate that differentiated cells were single cell-derived and MAPC are indeed "clonal" multipotent cells, cultures were made in which MAPC had been transduced with a retroviral vector and undifferentiated cells and their progeny were found to have the retrovirus inserted in the same site in the genome.

Studies were done using two independently derived ROSA26 MAPC, two C57BL/6 MAPC and one rMAPC population expanded for 40 to >90PDs, as well as with the eGFP transduced "clonal" mouse and "clonal" rMAPC. No differences were seen between eGFP transduced and untransduced cells. Of note, eGFP expression persisted in differentiated MAPC.

Specifically, murine and rat BMMNC cultured on FN with EGF, PDGF-BB and LIF for three weeks were transduced on two sequential days with an eGFP oncoretroviral vector. Afterwards, CD45+ and GlyA+ cells were depleted and cells sub-cultured at 10 cells/well. eGFP-transduced rat BMMNC were expanded for 85 PDs. Alternatively, mouse MAPC expanded for 80 PDS were used. Subcultures of undifferentiated MAPC were generated by plating 100 MAPC from cultures maintained for 75 PDs and re-expanding them to >5×10$^6$ cells. Expanded MAPC were induced to differentiate in vitro to endothelium, neuroectoderm and endoderm. Lineage differentiation was shown by staining with antibodies specific for these cell types.

Use in Animal MI Model

Rat MAPC cultures used in the studies were transduced by means of retroviral transduction with a green fluorescent protein marker. After the cells were transduced they were subcloned at 10 cells/well as described in PCT/US02/04652 (WO 02/064748) or PCT/US01/21387. The GFP-marked rat cultures that were used in these studies are clonally-derived as evidenced by identification of a single retroviral integration event in the expanded population. Moreover, as described in the PCT application, differentiation into the various cell types was performed on clonally-derived MAPC.

MAPCs have previously been shown to differentiate into cardiomyocyte-like cells and induce engraftment in cardiac tissue in animal studies (Jiang, Y. et al. (2002) Nature 418(6893): p. 41-9). Consequently, they likely hold potential to repair damage in the heart caused by myocardial infarction, congestive heart failure and vascular disorders.

Therapeutic benefit to repair damage in the heart caused by myocardial infarction, congestive heart failure and vascular disorders was evaluated in a Lewis rat model for myocardial infarction. Permanent ischemia is induced by direct surgical LAD ligation. The stem cells used in these experiments were isolated from the bone marrow of Sprague-Dawley (SD) rats and stably labeled by using a lentiviral construct encoding green fluorescent protein (GFP). In-vitro differentiation of the GFP-labeled MAPC into the endothelial (mesodermal), hepatic (endodermal), and neuronal (ectodermal) lineages and subsequent analysis of lineage specific marker expression by quantitative PCR (qPCR) confirmed that the GFP-labeled MAPCs had retained tri-lineage differentiation potential (FIG. 2). These stem cells were at population doubling numbers greater than 200 and displayed normal karyotypes and telomere lengths comparable to early bone marrow cultures.

To test the hypothesis that delivery of MAPCs to the myocardium in the peri-infarct region can help to improve cardiac function, Lewis rats received the MAPCs immediately after LAD ligation by direct injection into the infarct border zone (5 injections of 400,000 cells per injection). The study schema is shown in FIG. 3. This experiment was designed to show allogeneic cell use with secondary endpoints of benefit.

When echocardiography was performed at 2 weeks post-MI, a significant increase in shortening fraction was observed in those animals that received direct injection of MAPCs compared to the PBS vehicle control group (13.9±2.2% (n=4) vs. 24.0±6.6% (n=7), p<0.5, see FIG. 4). Shortening fraction is calculated as a percentage of end diastolic minus end systolic 2-D dimension, divided by end diastolic length.

Histological analysis of the heart tissue confirmed that all of the animals that displayed increased shortening fractions after stem cell injection had indeed undergone successful LAD ligation, as evidenced by the presence of extended zones of infarcted tissue in the left ventricular wall areas of the heart (FIG. 5). In addition, for all animals that received stem cells by direct myocardial injection, GFP positive MAPCs were identified in infarcted heart tissue and in the infarct border zones after immuno-fluorescence analysis (FIG. 5).

An absence of inflammatory lymphocytes in H & E sections of injected hearts that were positive for donor cells, either in the fibrotic ischemia zone or in healthy myocardium was observed (FIG. 5, B-D). In addition, no allogeneic Ab response could be detected using an serial dilutions of plasma against either donor stem cells or Sprague-Dawley splenocytes. Detection was performed using anti-rat kappa Ab, and controls against peripheral blood and isotype Ab showed the ability to detect all classes of rat immunoglobulin (data not shown). Mixed lymphocyte reactions (MLR) were performed, using collected blood cells at time of sacrifice against irradiated stem cells or Sprague Dawley splenocytes. No shift in peak MLR kinetics was seen in treated versus control animals, consistent with a lack of immune sensitization (data not shown). Phase II experiments include the use of rat aortic endothelial cells as a positive immune sensitizing population, and pre-immunization of recipient animals with Sprague-Dawley splenocytes as a positive control likely to show immune rejection.

These first observations are in support of the hypothesis that administering MAPCs to the injured heart can aid in improvement of heart function. This first experiment used a two-week endpoint, which is short in terms of assessing therapeutic benefit. Subsequent experiments are in progress with aims to evaluate dose-response characteristics and functional benefit assessment at a longer timescale, using a 6-week endpoint (FIG. 6). These second phase experiments all include testing the benefit of myocardial injection of MAPCs in acute MI models.

Immunogenicity of Human MAPC

Mesenchymal stem cells have demonstrated low in vitro immunogenicity, and the ability to engraft across in allogeneic recipients (Di Nicola, M et al (2002) Blood 99:3838-3843, Jorgensen, C. et al (2002) Gene Therapy 10:928-931, Le Blanc, K. et al (2003) Scandinavian Journal of Immunology 57:11-20, McIntosh, K. et al (2000) Graft 6:324-328, Tse, W. et al (2003) Transplantation 75:389-397).

FIG. 7 shows that human MAPCs exhibit low in vitro immunogenicity, and, analogous to mesenchymal stem cells, are immunosuppressive when added to otherwise potent T cell MLR (Tse, W., et al (2003) Transplantation 75:389-397). Responder and stimulator cells were prepared, and MLRs performed, according to procedures described by Tse, W. et al (Transplantation 75:389-397)). Results are consistent across all donor and responder pairs tested. Accordingly, MAPCs are useful in both syngeneic and allogeneic applications for the purposes described above, including providing cardiomyocytes, providing myocardium, providing cardiac muscle, providing systolic and/or diastolic function, treating MI, treating CHF, and the like, either directly by in situ differentiation or indirectly, by secreting factors that act on other cells to provide these results.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of providing cardiac muscle to a subject in need thereof, said method comprising administering to the subject, in an amount effective to provide new cardiac muscle, isolated expanded human multipotent non-ES, non-germ cells that express telomerase, have the capacity to undergo 40 cell doublings in culture and have a normal karyotype, wherein the existing cardiac muscle is damaged by disease or injury.

2. The method of claim 1 wherein the non-embryonic, non-germ cells further express one or more of oct4, rex-1, rox-1, or sox-2.

3. The method of either of claims 1 or 2, wherein the disease is selected from the group consisting of congestive heart failure, coronary artery disease, myocardial infarction, myocardial ischemia, atherosclerosis, cardiomyopathy, idiopathic cardiomyopathy, cardiac arrhythmias, muscular dystrophy, muscle mass abnormality, muscle degeneration, infective myocarditis, drug- or toxin-induced muscle abnormalities, hypersensitivity myocarditis, autoimmune endocarditis, and congenital heart disease.

4. The method of claim 1 wherein the cells are derived from bone marrow.

5. The method of claim 1 wherein the cells have undergone 10-40 cell doublings in culture.

6. The method of claim 1 wherein the cells can differentiate into at least one cell type of at least two of the endodermal, ectodermal and mesodermal embryonic lineages.

7. The method of claim 6 wherein the cells can differentiate into at least one cell type of each of the endodermal, ectodermal, and mesodermal embryonic lineages.

* * * * *